US00RE42130E

(19) United States
(12) Reissued Patent
Bowdish et al.

(10) Patent Number: US RE42,130 E
(45) Date of Reissued Patent: Feb. 8, 2011

(54) PHAGEMID VECTORS

(75) Inventors: Katherine S. Bowdish, Del Mar, CA (US); Shana Frederickson, Solana Beach, CA (US); Martha Wild, San Diego, CA (US)

(73) Assignee: Alexion Pharmaceuticals, Inc., Cheshire, CT (US)

(21) Appl. No.: 11/986,963

(22) Filed: Nov. 26, 2007

Related U.S. Patent Documents

Reissue of:
(64) Patent No.: 6,803,230
Issued: Oct. 12, 2004
Appl. No.: 10/134,188
Filed: Apr. 26, 2002

U.S. Applications:
(60) Provisional application No. 60/287,355, filed on Apr. 27, 2001.

(51) Int. Cl.

| | |
|---|---|
| ***C12N 15/63*** | (2006.01) |
| ***C12N 15/70*** | (2006.01) |
| ***C12N 15/73*** | (2006.01) |
| ***C12N 15/64*** | (2006.01) |
| ***C12N 15/65*** | (2006.01) |
| ***C07H 21/04*** | (2006.01) |

(52) U.S. Cl. ..... 435/320.1; 536/23.1; 536/23.4; 536/23.7; 536/24.1; 536/23.2; 435/69.1; 435/5

(58) Field of Classification Search ..... None
See application file for complete search history.

(56) References Cited

U.S. PATENT DOCUMENTS

| | | | |
|---|---|---|---|
| 5,658,727 | A | 8/1997 | Barbas et al. |
| 6,113,896 | A | 9/2000 | Lazarus et al. |
| 6,346,394 | B1 | 2/2002 | Mitsuzumi et al. |

FOREIGN PATENT DOCUMENTS

| | | | |
|---|---|---|---|
| WO | WO-95/11317 | | 4/1995 |
| WO | WO-2000/71694 | A1 | 11/2000 |
| WO | WO-2004/078937 | A2 | 9/2004 |

OTHER PUBLICATIONS

Mattanovich et al. Optimization of recombinant gene expression in Escherichia coli. Annals of the New York Academy of Sciences, vol. 782, pp. 182–190, 1996.*
Alting–Mees, Ma et al., Methods in Enzymology "PBluescriptll: multifunctional cloning and mapping vectors", vol. 216, pp. 483–495 (1992).
Barbas III et al., "Pharge Display: A Laboratory Manual", Cold Spring Harbor Press, (2001).
Genbank Entry Number AF268280.1 (sequence of pComb3H vector) available on National Center fro Biological Information database (2000).
Genbank Entry Number AF268280.1 (sequence of pComb3X vector) available on National Center fro Biological Information database (2000).
Krebber, A. et al., Inclusion of an upstream transcriptional terminator in phage display vector abolishes background expression of toxic fusions with coat protein g3p Gene, 178 (1996) 71–74.
Lewin, Gene, Chapter 13, pp. 202–216 (1983).
Mamoru, W. et al., Protein Expression and Purification, "Overproduction of D–Aminoaclase from Alcalugenes xylosoxydans subsp. xylosoxydans A–6 in Escherichia coli and Its Purification", 7: 395–389 (1996).
Map of pComb3H vector. printed in 2006.
Map of pComb3X vector.printed in 2006.
Print–out from Amazon.com website showing publication of Chapter 2 of "Phage Display: A Laboratory Manual", dated Jan. 15, 2001.
Rader, C. et al., Current Opinion in Biotechnology "Phage Display of Combinatorial Antibody Libraries", 8: 503–508 (1997).
Table of features of pComb3X and pComb3H vectors relative of claim 1 of EP–B–1390489, 2006.
Weiss, Ga et al., JMB, "Design and Evolution of Artificial M13 Coat Proteins", 300: 213–219 (2000).
Zimmerman et al., Protein Expression and Purification, "High–Level Expression of Rat Farnesyl: Protein Transferase in Escherichia Coli as a Translationally Coupled Heterodimer", 14: 395–402 (1998).
Gao et al., "Making artificial antibodies: A format for phage display of combinatorial heterodimeric arrays", Proc. National Acad. Sci. USA, vol. 96, pp. 6025–6030 (1999).
Gao et al., "Making chemistry selectable by linking it to infectivity", Proc. National Acad. Sci. USA, vol. 94, pp. 11777–11782 (1997).
Minute of the Oral Proceedings in EP Patent No. B–1390489 (App. No. 02 734 056.1) dated Dec. 17, 2008.
Krebber et al., Gene, 1996, vol. 178, pp. 71–74.*
"Genes", Benjamin Lewis, Ed., John Wiley & Sons, Inc., Chapter 13, "Termination and Antitermination", pp. 202–216.*

* cited by examiner

*Primary Examiner*—Jennifer Dunston
(74) *Attorney, Agent, or Firm*—Ropes & Gray LLP

(57) ABSTRACT

Phagemid vectors containing a sequence of features between a Col E1 origin and an f1 origin are useful for display of polypeptides or proteins, including antibody libraries.

3 Claims, 46 Drawing Sheets

ATCCAGTCTATTAATTGTTGCCGGGAAGCTAGAGTAAGTAGTTCGCCAGTTAATAGTTTGCGCAACGTTGTTGCCATTGCTACAGGCATCGTGGTGTCAC 2000 beta lactamase

GCTCGTCGTTTGGTATGGCTTCATTCAGCTCCGGTTCCCAACGATCAAGGCGAGTTACATGATCCCCCATGTTGTGCAAAAAAGCGGTTAGCTCCTTCGG 2100 beta lactamase

Pvu I

TCCTCCGATCGTTGTCAGAAGTAAGTTGGCCGCAGTGTTATCACTCATGGTTATGGCAGCACYGCATAATTCTCTTACTGTCATGCCATCCGTAAGATGC 2200 beta lactamase

TTTTCTGTGACTGGTGAGTACTCAACCAAGTCATTCTGAGAATAGTGTATGCGGCGACCGAGTTGCTCTTGCCCGGCGTCAATACGGGATAATACCGCGC 2300 beta lactamase

CACATAGCAGAACTTTAAAAGTGCTCATCATTGGAAAACGTTCTTCGGGGCGAAAACTCTCAAGGATCTTACCGCTGTTGAGATCCAGTTCGATGTAACC 2400 beta lactamase

CACTCGTGCACCCAACTGATCTTCAGCATCTTTTACTTTCACCAGCGTTTCTGGGTGAGCAAAAACAGGAAGGCAAAATGCCGCAAAAAAGGGAATAAGG 2500 beta lactamase

*FIG. 4b (Cont.)*

GCGACACGGAAATGTTGAATACTCATACTCTTCCTTTTTCAATATTATTGAAGCATTTATCAGGGTTATTGTCTCATGAGCGGATACATATTTGAATGTA 2600 beta lactamase

TTTAGAAAAATAAACAAATAGGGGTTCCGCGCACATTTCCCCGAAAAGTGCCAC 2654

*FIG. 4c*

(Seq. ID No. 20)

CTAAATTGTAAGCGTTAATATTTTGTTAAAATTCGCGTTAAATTTTTGTTAAATCAGCTCATTTTTTAACCAATAGGCCGAAATCGGCAAAATCCCTTAT 100 f1 origin

AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA 200 f1 origin

CCGTCTATCAGGGCGATGGCCCACTACGTGAACCATCACCCTAATCAAGTTTTTTGGGGTCGAGGTGCCGTAAAGCACTAAATCGGAACCCTAAAGGGAG 300 f1 origin

CCCCCGATTTAGAGCTTGACGGGGAAAGCCGGCGAACGTGGCGAGAAAGGAAGGGAAGCGAAAGGAGCGGGCGCTAGGGCGCTGGCAAGTGTAGCG 400 f1 origin

Pvu I

GTCACGCTGCGCGTAACCACCACACCCGCCGCGCTTAATGCGCCGCTACAGGGCGCGTCCCATTCGCCATTCAGGCTGCGCAACTGTTGGGAAGGGCGAT 500 f1 origin

Not I EcoR I

CGGTAATGCGGCCGCTACATGAATTCAATTGTTATCCGCTCACAATTCCACACAACATACGAGCCGGGAGCATAAAGTGTAAAGCCTGGGGTGCCTAATG 600 lac rep lac

*FIG. 6a*

TCGTGTAGATAACTACGATACGGGAGGGCTTACCATCTGGCCCCAGTGCTGCAATGATACCGCGAGACCCACGCTCACCGGCTCCAGATTTATCAGCAAT 1900

AAACCAGCCAGCCGGAAGGGCCGAGCGCAGAAGTGGTCCTGCAACTTTATCCGCCTCCATCCAGTCTATTAATTGTTGCCGGGAAGCTAGAGTAAGTAGT 2000

TCGCCAGTTAATAGTTTGCGCAACGTTGTTGCCATTGCTACAGGCATCGTGGTGTCACGCTCGTCGTTTGGTATGGCTTCATTCAGCTCCGGTTCCCAAC 2100

Pvu I

GATCAAGGCGAGTTACATGATCCCCCATGTTGTGCAAAAAAGCGGTTAGCTCCTTCGGTCCTCCGATCGTTGTCAGAAGTAAGTTGGCCGCAGTGTTATC 2200

ACTCATGGTTATGGCAGCACTGCATAATTCTCTTACTGTCATGCCATCCGTAAGATGCTTTTCTGTGACTGGTGAGTACTCAACCAAGTCATTCTGAGAA 2300

TAGTGTATGCGGCGACCGAGTTGCTCTTGCCCGGCGTCAATACGGGATAATACCGCGCCACATAGCAGAACTTTAAAAGTGCTCATCATTGGAAAACGTT 2400

CTTCGGGGCGAAAACTCTCAAGGATCTTACCGCTGTTGAGATCCAGTTCGATGTAACCCACTCGTGCACCCAACTGATCTTCAGCATCTTTTACTTTCAC 2500

*FIG. 6b (Cont.)*

CAGCGTTTCTGGGTGAGCAAAAACAGGAAGGCAAAATGCCGCAAAAAAGGGAATAAGGGCGACACGGAAATGTTGAATACTCATACTCTTCCTTTTTCAA 2600

TATTATTGAAGCATTTATCAGGGTTATTGTCTCATGAGCGGATACATATTTGAATGTATTTAGAAAAATAAACAAATAGGGGTTCCGCGCACATTTCCCC 2700

GAAAAGTGCCAC 2712

*FIG. 6c*

(Seq. ID No. 21)

GTGGCACTTTTCGGGGAAATGTGCGCGGAACCCCTATTTGTTTATTTTTCTAAATACATTCAAATATGTATCCGCTCATGAGACAATAACCCTGATAAAT 100

GCTTCAATAATATTGAAAAAGGAAGAGTATGAGTATTCAACATTTCCGTGTCGCCCTTATTCCCTTTTTTGCGGCATTTTGCCTTCCTGTTTTTGCTCAC 200 beta lactamase

CCAGAAACGCTGGTGAAAGTAAAAGATGCTGAAGATCAGTTGGGTGCACGAGTGGGTTACATCGAACTGGATCTCAACAGCGGTAAGATCCTTGAGAGTT 300 beta lactamase

TTCGCCCCGAAGAACGTTTTCCAATGATGAGCACTTTTAAAGTTCTGCTATGTGGCGCGGTATTATCCCGTATTGACGCCGGGCAAGAGCAACTCGGTCG 400 beta lactamase

CCGCATACACTATTCTCAGAATGACTTGGTTGAGTACTCACCAGTCACAGAAAAGCATCTTACGGATGGCATGACAGTAAGAGAATTATGCAGTGCTGCC 500 beta lactamase

Pvu I

ATAACCATGAGTGATAACACTGCGGCCAACTTACTTCTGACAACGATCGGAGGACCGAAGGAGCTAACCGCTTTTTTGCACAACATGGGGGATCATGTAA 600 beta lactamase

*FIG. 8a*

CTCGCCTTGATCGTTGGGAACCGGAGCTGAATGAAGCCATACCAAACGACGAGCGTGACACCACGATGCCTGTAGCAATGGCAACAACGTTGCGCAAACT 700 beta lactamase

ATTAACTGGCGAACTACTTACTCTAGCTTCCCGGCAACAATTAATAGACTGGATGGAGGCGGATAAAGTTGCAGGACCACTTCTGCGCTCGGCCCTTCCG 800 beta lactamase

GCTGGCTGGTTTATTGCTGATAAATCTGGAGCCGGTGAGCGTGGGTCTCGCGGTATCATTGCAGCACTGGGGCCAGATGGTAAGCCCTCCCGTATCGTAG 900 beta lactamase

TTATCTACACGACGGGGAGTCAGGCAACTATGGATGAACGAAATAGACAGATCGCTGAGATAGGTGCCTCACTGATTAAGCATTGGTAACTGTCAGACCA 1000 beta lactamase

AGTTTACTCATATATACTTTAGATTGATTTAAAACTTCATTTTTAATTTAAAAGGATCTAGGTGAAGATCCTTTTTGATAATCTCATGACCAAAATCCCT 1100

TAACGTGAGTTTTCGTTCCACTGAGCGTCAGACCCCGTAGAAAAGATCAAAGGATCTTCTTGAGATCCTTTTTTTCTGCGCGTAATCTGCTGCTTGCAAA 1200 col E1

CAAAAAAACCACCGCTACCAGCGGTGGTTTGTTTGCCGGATCAAGAGCTACCAACTCTTTTTCCGAAGGTAACTGGCTTCAGCAGAGCGCAGATACCAAA 1300 col E1

*FIG. 8a (Cont.)*

CAAACCGCCTCTCCCCGCGCGTTGGCCGATTCATTAATGCAGCTGGCACGACAGGTTTCCCGACTGGAAAGCGGGCAGTGAGCGCAACGCAATTAATGTG 2100 lac

EcoR I Xba I

AGTTAGCTCACTCATTAGGCACCCCAGGCTTTACACTTTATGCTCCCGGCTCGTATGTTGTGTGGAATTGTGAGCGGATAACAATTGAATTCACATCTAG 2200 lac rep

Xho I Spe I Sfi I Not I Pvu I

ATATCTCGAGTCAATACTAGTGGCCAGGCCGGCCAGCGGCCGCATTACCGATCGCCCTTCCCAACAGTTGCGCAGCCTGAATGGCGAATGGGACGCGCCC 2300 f1 origin

TGTAGCGGCGCATTAAGCGCGGCGGGTGTGGTGGTTACGCGCAGCGTGACCGCTACACTTGCCAGCGCCCTAGCGCCCGCTCCTTTCGCTTTCTTCCCTT 2400 f1 origin

CCTTTCTCGCCACGTTCGCCGGCTTTCCCCGTCAAGCTCTAAATCGGGGGCTCCCTTTAGGGTTCCGATTTAGTGCTTTACGGCACCTCGACCCCAAAAA 2500 f1 origin

ACTTGATTAGGGTGATGGTTCACGTAGTGGGCCATCGCCCTGATAGACGGTTTTTCGCCCTTTGACGTTGGAGTCCACGTTCTTTAATAGTGGACTCTTG 2600 f1 origin

TTCCAAACTGGAACAACACTCAACCCTATCTCGGTCTATTCTTTTGATTTATAAGGGATTTTGCCGATTTCGGCCTATTGGTTAAAAAATGAGCTGATTT 2700 f1 origin

*FIG. 8b (Cont.)*

Seq. ID No. 18

GTGGCACTTTTCGGGGAAATGTGCGCGGAACCCCTATTTGTTTATTTTTCTAAATACATTCAAATATGTATCCGCTCATGAGACAATAACCCTGATAAAT 100

Ear I

GCTTCAATAATATTGAAAAAGGAAGAGTATGAGTATTCAACATTTCCGTGTCGCCCTTATTCCCTTTTTTGCGGCATTTTGCCTTCCTGTTTTTGCTCAC 200 beta lactamase

CCAGAAACGCTGGTGAAAGTAAAAGATGCTGAAGATCAGTTGGGTGCACGAGTGGGTTACATCGAACTGGATCTCAACAGCGGTAAGATCCTTGAGAGTT 300 beta lactamase

TTCGCCCCGAAGAACGTTTTCCAATGATGAGCACTTTTAAAGTTCTGCTATGTGGCGCGGTATTATCCCGTATTGACGCCGGGCAAGAGCAACTCGGTCG 400 beta lactamase

CCGCATACACTATTCTCAGAATGACTTGGTTGAGTACTCACCAGTCACAGAAAAGCATCTTACGGATGGCATGACAGTAAGAGAATTATGCAGTGCTGCC 500 beta lactamase

ATAACCATGAGTGATAACACTGCGGCCAACTTACTTCTGACAACGATCGGAGGACCGAAGGAGCTAACCGCTTTTTTGCACAACATGGGGGATCATGTAA 600 beta lactamase

*FIG. 11a*

AGGGCTGTCTGTGGAATGCTACAGGCGTTGTAGTTTGTACTGGTGACGAAACTCAGTGTTACGGTACATGGGTTCCTATTGGGCTTGCTATCCCTGAAAA 2600 f1 gIII

TGAGGGTGGTGGCTCTGAGGGTGGCGGTTCTGAGGGTGGCGGCTCTGAGGGTGGCGGTACTAAACCTCCTGAGTACGGTGATACACCTATTCCGGGCTAT 2700 f1 gIII

ACTTATATCAACCCTCTCGACGGCACTTATCCGCCTGGTACTGAGCAAAACCCCGCTAATCCTAATCCTTCTCTTGAGGAGTCTCAGCCTCTTAATACTT 2800 f1 gIII

TCATGTTTCAGAATAATAGGTTCCGAAATAGGCAGGGGGCATTAACTGTTTATACGGGCACTGTTACTCAAGGCACTGACCCCGTTAAAACTTATTACCA 2900 f1 gIII

GTACACTCCTGTATCATCAAAAGCCATGTATGACGCTTACTGGAACGGTAAATTCAGAGACTGCGCTTTCCATTCTGGCTTTAATGAGGATCCATTCGTT 3000 f1 gIII

TGTGAATATCAAGGCCAATCGTCTGACCTGCCTCAACCTCCTGTTAATGCTGGCGGCGGCTCTGGTGGTGGTTCTGGTGGCGGCTCTGAGGGTGGTGGCT 3100 f1 gIII

CTGAGGGTGGCGGTTCTGAGGGTGGCGGCTCTGAGGGTGGCGGTTCCGGTGGTGGCTCTGGTTCCGGTGATTTTGATTATGAAAAGATGGCAAACGCTAA 3200 f1 gIII

*FIG. 11c*

(SEQ. ID NO. 29)
XhoI
CTCGAGCTGATGAGCCATGGAAGCTGTGTCGCCTGCACCAGGCTCCCACGGCTCGTGGTGCGGTGCGCTTCTGGTGTTCGCTGCCTACAGCCGACACGTC 100
stuffer
GAGCTTCGTGCCCCTAGAGTTGCGCGTCACAGCAGCCTCCGGCGCTCCGCGATATCACCGTGTCATCCACATCAATGAAGTAGTGCTCCTAGACGCCCCC 200
stuffer
GTGGGGCTGGTGGCGCGGTTGGCTGACGAGAGCGGCCACGTAGTGTTGCGCTGGCTCCCGCCGCCTGAGACACCCATGACGTCTCACATCCGCTACGAGG 300
stuffer
TGGACGTCTCGGCCGGCAACGGCGCAGGGAGCGTACAGAGGGTGGAGATCCTGGAGGGCCGCACCGAGTGTGTGCTGAGCAACCTGCGGGGCCGGACGCG 400
stuffer
CTACACCTTCGCCGTCCGCGCGCGTATGGCTGAGCCGAGCTTCGGCGGCTTCTGGAGCGCCTGGTCGGAGCCTGTGTCGCTGCTGACGCCTAGCGACCTG 500
stuffer
GACCCCTCATCCTGACGCTCTCCCTCATCCTCGTGGTCATCCTGGTGCTGCTGACCGTGCTCGCGCTGCTCTCCCACCGCCGGGCTCTGAAGCAGAAGA 600
stuffer
TCTGGCCTGGCATCCCGAGCCCAGAGAGCGAGTTTGAAGGCCTCTTCACCACCCACAAGGGTAACTTCCAGCTGTGGCTGTACCAGAATGATGGCTGCCT 700
stuffer

*FIG. 12F*

(SEQ. ID NO. 30)
XhoI
CTCGAGCTGATGAGCCATGGAAGCTGTGTCGCCTGCACCAGGCTCCCACGGCTCGTGGTGCGGTGCGCTTCTGGTGTTCGCTGCCTACAGCCGACACGTC 100
stuffer
GAGCTTCGTGCCCCTAGAGTTGCGCGTCACAGCAGCCTCCGGCGCTCCGCGATATCACCGTGTCATCCACATCAATGAAGTAGTGCTCCTAGACGCCCCC 200
stuffer
GTGGGGCTGGTGGCGCGGTTGGCTGACGAGAGCGGCCACGTAGTGTTGCGCTGGCTCCCGCGCCTGAGACACCCATGACGTCTCACATCCGCTACGAGG 300
stuffer
TGGACGTCTCGGCCGGCAACGGCGCAGGAGCGTACAGAGGGTGGAGATCCTGGAGGGCCGCACCGAGTGTGCTGAGCAACCTGCGGGGCCGGACGCG 400
stuffer
CTACACCTTCGCCGTCCGCGCGCGTATGGCTGAGCCGAGCTTCGGCGGCTTCTGGAGCGCCTGGTCGGAGCCTGTGTCGCTGCTGACGCCTAGCGACCTG 500
stuffer
GACCCCCTCATCCTGACGCTCTCCCTCATCCTCGTGGTCATCCTGGTGCTGCTGACCGTGCTCGCGCTGCTCTCCCACCGCCGGGCTCTGAAGCAGAAGA 600
stuffer
TCTGGCCTGGCATCCCGAGCCCAGAGAGCGAGTTTGAAGGCCTCTTCACCACCCACAAGGGTAACTTCCAGCTGTGGCTGTACCAGAATGATGGCTGCCT 700
stuffer

*FIG. 12G*

(SEQ. ID NO. 31)

GTGGCACTTTTCGGGGAAATGTGCGCGGAACCCCTATTTGTTTATTTTTCTAAATACATTCAAATATGTATCCGCTCATGAGACAATAACCCTGATAAAT 100

GCTTCAATAATATTGAAAAAGGAAGAGTATGAGTATTCAACATTTCCGTGTCGCCCTTATTCCCTTTTTTGCGGCATTTTGCCTTCCTGTTTTTGCTCAC 200 beta lactamase

CCAGAAACGCTGGTGAAAGTAAAAGATGCTGAAGATCAGTTGGGTGCACGAGTGGGTTACATCGAACTGGATCTCAACAGCGGTAAGATCCTTGAGAGTT 300 beta lactamase

TTCGCCCCGAAGAACGTTTTCCAATGATGAGCACTTTTAAAGTTCTGCTATGTGGCGCGGTATTATCCCGTATTGACGCCGGGCAAGAGCAACTCGGTCG 400 beta lactamase

CCGCATACACTATTCTCAGAATGACTTGGTTGAGTACTCACCAGTCACAGAAAAGCATCTTACGGATGGCATGACAGTAAGAGAATTATGCAGTGCTGCC 500 beta lactamase

ATAACCATGAGTGATAACACTGCGGCCAACTTACTTCTGACAACGATCGGAGGACCGAAGGAGCTAACCGCTTTTTTGCACAACATGGGGGATCATGTAA 600 beta lactamase

CTCGCCTTGATCGTTGGGAACCGGAGCTGAATGAAGCCATACCAAACGACGAGCGTGACACCACGATGCCTGTAGCAATGGCAACAACGTTGCGCAAACT 700 beta lactamase

*FIG. 13A*

ATTAACTGGCGAACTACTTACTCTAGCTTCCCGGCAACAATTAATAGACTGGATGGAGGCGGATAAAGTTGCAGGACCACTTCTGCGCTCGGCCCTTCCG 800 beta lactamase

GCTGGCTGGTTTATTGCTGATAAATCTGGAGCCGGTGAGCGTGGGTCTCGCGGTATCATTGCAGCACTGGGGCCAGATGGTAAGCCCTCCCGTATCGTAG 900 beta lactamase

TTATCTACACGACGGGGAGTCAGGCAACTATGGATGAACGAAATAGACAGATCGCTGAGATAGGTGCCTCACTGATTAAGCATTGGTAACTGTCAGACCA 1000 beta lactamase

AGTTTACTCATATATACTTTAGATTGATTTAAAACTTCATTTTTAATTTAAAAGGATCTAGGTGAAGATCCTTTTTGATAATCTCATGACCAAAATCCCT 1100

TAACGTGAGTTTTCGTTCCACTGAGCGTCAGACCCCGTAGAAAAGATCAAAGGATCTTCTTGAGATCCTTTTTTTCTGCGCGTAATCTGCTGCTTGCAAA 1200 col E1

CAAAAAAACCACCGCTACCAGCGGTGGTTTGTTTGCCGGATCAAGAGCTACCAACTCTTTTTCCGAAGGTAACTGGCTTCAGCAGAGCGCAGATACCAAA 1300 col E1

TACTGTCCTTCTAGTGTAGCCGTAGTTAGGCCACCACTTCAAGAACTCTGTAGCACCGCCTACATACCTCGCTCTGCTAATCCTGTTACCAGTGGCTGCT 1400 col E1

GCCAGTGGCGATAAGTCGTGTCTTACCGGGTTGGACTCAAGACGATAGTTACCGGATAAGGCGCAGCGGTCGGGCTGAACGGGGGGTTCGTGCACACAGC 1500 col E1

*FIG. 13A (Cont.)*

TAATACTTTCATGTTTCAGAATAATAGGTTCCGAAATAGGCAGGGGGCATTAACTGTTTATACGGGCACTGTTACTCAAGGCACTGACCCCGTTAAAACT 2900 f1 gIII

TATTACCAGTACACTCCTGTATCATCAAAAGCCATGTATGACGCTTACTGGAACGGTAAATTCAGAGACTGCGCTTTCCATTCTGGCTTTAATGAGGATC 3000 f1 gIII

CATTCGTTTGTGAATATCAAGGCCAATCGTCTGACCTGCCTCAACCTCCTGTTAATGCTGGCGGCGGCTCTGGTGGTGGTTCTGGTGGCGGCTCTGCGGG 3100 f1 gIII

TGGTGGCTCTGAGGGTGGCGGTTCTGAGGGTGGCGGCTCTGAGGGTGGCGGTTCCGGTGGTGGCTCTGGTTCCGGTGATTTTGATTATGAAAAGATGGCA 3200 f1 gIII

AACGCTAATAAGGGGGCTATGACCGAAAATGCCGATGAAAACGCGCTACAGTCTGACGCTAAAGGCAAACTTGATTCTGTCGCTACTGATTACGGTGCTG 3300 f1 gIII

CTATCGACGGTTTCATTGGTGACGTTTCCGGCCTTGCTAATGGTAATGGTGCTACTGGTGATTTTGCTGGCTCTAATTCCCAAATGGCTCAAGTCGGTGA 3400 f1 gIII

CGGTGATAATTCACCTTTAATGAATAATTTCCGTCAATATTTACCTTCCCTCCCTCAATCGGTTGAATGTCGCCCTTTTGTCTTTGGCGCTGGTAAACCA 3500 f1 gIII

TATGAATTTTCTATTGATTGTGACAAAATAAACTTATTCCGTGGTGTCTTTGCGTTTCTTTTATATGTTGCCACCTTTATGTATGTATTTTCGACGTTTG 3600 f1 gIII

*FIG. 13C*

PHAGEMID VECTORS

Matter enclosed in heavy brackets [ ] appears in the original patent but forms no part of this reissue specification; matter printed in italics indicates the additions made by reissue.

This application claims priority under 35 USC 119(e) to provisional application 60/287,355, filed Apr. 27, 2001.

BACKGROUND

1. Technical Field

This disclosure relates to cloning vectors. More specifically, phagemid vectors useful in the cloning and expression of foreign genetic information are disclosed.

2. Background of Related Art

Plasmids are extrachromosomal genetic elements capable of autonomous replication within their hosts. Bacterial plasmids range in size from 1 Kb to 200 Kb or more and encode a variety of useful properties. Plasmid encoded traits include resistance to antibiotics, production of antibiotics, degradation of complex organic molecules, production of bacteriocins, such as colicins, production of enterotoxins, and production of DNA restriction and modification enzymes.

Although plasmids have been studied for a number of years in their own right, particularly in terms of their replication, transmissibility, structure and evolution, with the advent of genetic engineering technology the focus of plasmid research has turned to the use of plasmids as vectors for the cloning and expression of foreign genetic information. In its application as a vector, the plasmid should possess one or more of the following properties. The plasmid DNA should be relatively small but capable of having relatively large amounts of foreign DNA incorporated into it. The size of the DNA insert is of concern in vectors based on bacteriophages where packing the nucleic acid into the phage particles can determine an upper limit. The plasmid should be under relaxed replication control. That is, where the replication of the plasmid molecule is not strictly coupled to the replication of the host DNA (stringent control), thereby resulting in multiple copies of plasmid DNA per host cell. The plasmid should express one or more selectable markers, such as the drug resistance markers, mentioned above, to permit the identification of host cells which contain the plasmid and also to provide a positive selection pressure for the maintenance of the plasmid in the host cell. Finally the plasmid should contain a single restriction site for one or more endonucleases in a region of plasmid which is not essential for plasmid replication. A vector as described above is useful, for example, for cloning genetic information, by which is meant integrating a segment of foreign DNA into the vector and reproducing identical copies of that information by virtue of the replication of the plasmid DNA.

The next step in the evolution of vector technology was the construction of so-called expression vectors. These vectors are characterized by their ability not only to replicate the inserted foreign genetic information but also to promote the transcription of the genetic information into mRNA and its subsequent translation into protein. This expression requires a variety of regulatory genetic sequences including but not necessarily limited to promoters, operators, transcription terminators, ribosomal binding sites and protein synthesis initiation and termination codons. These expression elements can be provided with the foreign DNA segment as parts thereof or can be integrated within the vector in a region adjacent to a restriction site so that when a foreign DNA segment is introduced into the vector it falls under the control of those elements to which it is now chemically joined.

Filamentous bacteriophage consist of a circular, single-stranded DNA molecule surrounded by a cylinder of coat proteins. There are about 2,700 molecules of the major coat proteins pVIII that envelope the phage. At one end of the phage particle, there are approximately five copies of each of gene III and VI proteins (pIII and pVI) that are involved in host cell binding and in the termination of the assembly process. The other end contains five copies of each of pVII and pIX that are required for the initiation of assembly and for maintenance of virion stability. In recent years, vectors have been developed and utilized for the display of foreign peptides and proteins on the surface of filamentous phage or phagemid particles.

The display of peptides and proteins on the surface of phage or phagemid particles represents a powerful methodology for selection of rare members in a complex library and for carrying out molecular evolution in the laboratory. The ability to construct libraries of enormous molecular diversity and to select for molecules with predetermined properties has made this technology applicable to a wide range of problems. A few of the many applications of such technology are: i) phage display of natural peptides including, mapping epitopes of monoclonal and polyclonal antibodies and generating immunogens; ii) phage display of random peptides, including mapping epitopes of monoclonal and polyclonal antibodies, identifying peptide ligands, and mapping substrate sites for proteases and kinases; and iii) phage display of protein and protein domains, including directed evolution of proteins, isolation of antibodies and cDNA expression screening.

Vectors have been developed which incorporate DNA from plasmids and bacteriophage. These phagemid vectors are derived by modifications of a plasmid genome containing an origin of replication from a bacteriophage, (e.g. f1, M13, fd) as well as the plasmid origin of replication. Phagemids are useful for the expression of foreign genetic information.

One known phagemid vector is [pBluescript] *PBLUESCRIPT*™ II KS+ (pBS II KS+) (Stratagene, La Jolla, Calif.), which is a useful starting point for the construction of the present vector because of its small size and the fact that it contains the colE1 plasmid origin of replication and the phage f1 origin of replication in the desired orientation. The plasmid also carries an ampicillin resistance gene.

Vectors which due to their structures provide enhanced functionality would be desirable.

SUMMARY

Novel plasmid vectors capable of replication and expression of foreign genetic information in bacteria, such as, for example, cyanobacterium and E. coli are described herein. These new vectors contain a specific sequence of features after the ColE1 origin but before the f1 origin. Specifically, the present phagemid vector contains, after the ColE1 origin but before the f1 origin, a bacterial transcription terminator, a promoter, a first ribosomal binding site, a first leader sequence and a first cloning region, a second ribosomal binding site, a second leader sequence and a second cloning region. The second cloning region is adapted to receive a gene encoding a polypeptide to be displayed and a nucleotide sequence encoding at least a functional domain of a display protein.

The vectors described herein are constructed through a series of steps which convert a starting vector through a series of intermediate plasmids to the present novel vector which can be used for display of antibody libraries.

BRIEF DESCRIPTION OF THE DRAWINGS

FIGS. 4A–C show the sequence (Seq. ID No. 19) of intermediate vector p110-81.6;

FIGS. 6A–C show the sequence (Seq. ID No. 20) of intermediate vector p131-03.7;

FIGS. 8A–C show the sequence (Seq. ID No. 21) of intermediate vector p131-39.1;

FIGS. 12A–G show the nucleic acid sequences of illustrative stuffer sequences.

FIGS. 13A–C show the nucleic acid sequence of plasmid pAX131 Xba/Not.

DETAILED DESCRIPTION OF PREFERRED EMBODIMENTS

Figure 1:
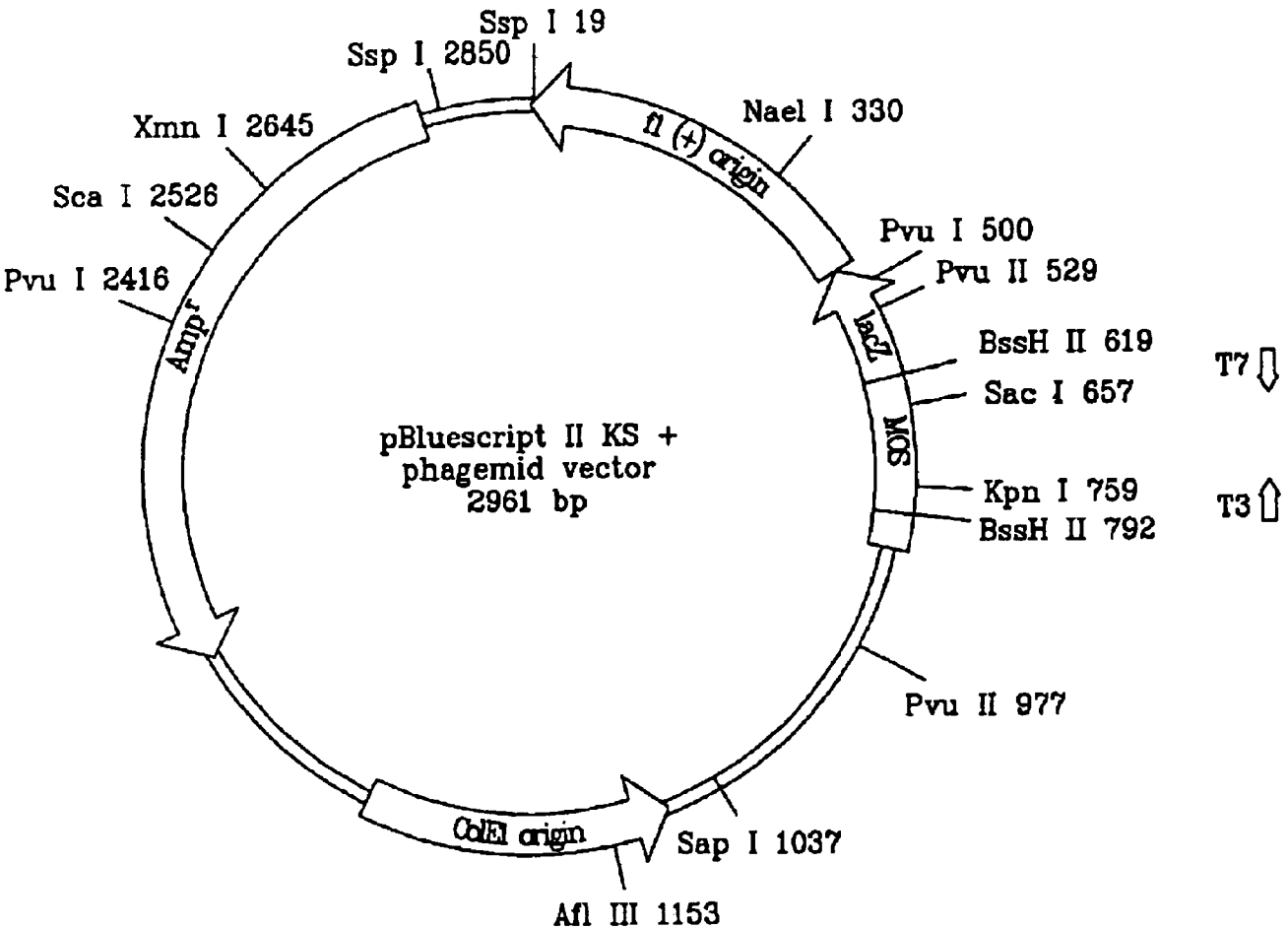
FIG. 1 schematically illustrates the structure of pBS II KS+, a useful starting vector for making the novel vectors described herein.

The present novel phagemid vectors are useful for display of polypeptides such as, for example, antibody libraries. The vectors described herein can be prepared using any commercially available vector containing a ColE1 and an f1 origin of replication as the starting material. Such starting materials are known and are commercially available. One suitable starting material is the vector pBS II KS+ which is commercially available from Stratagene Corp., La Jolla, Calif. (Sec FIG. 1).

Figure 2:
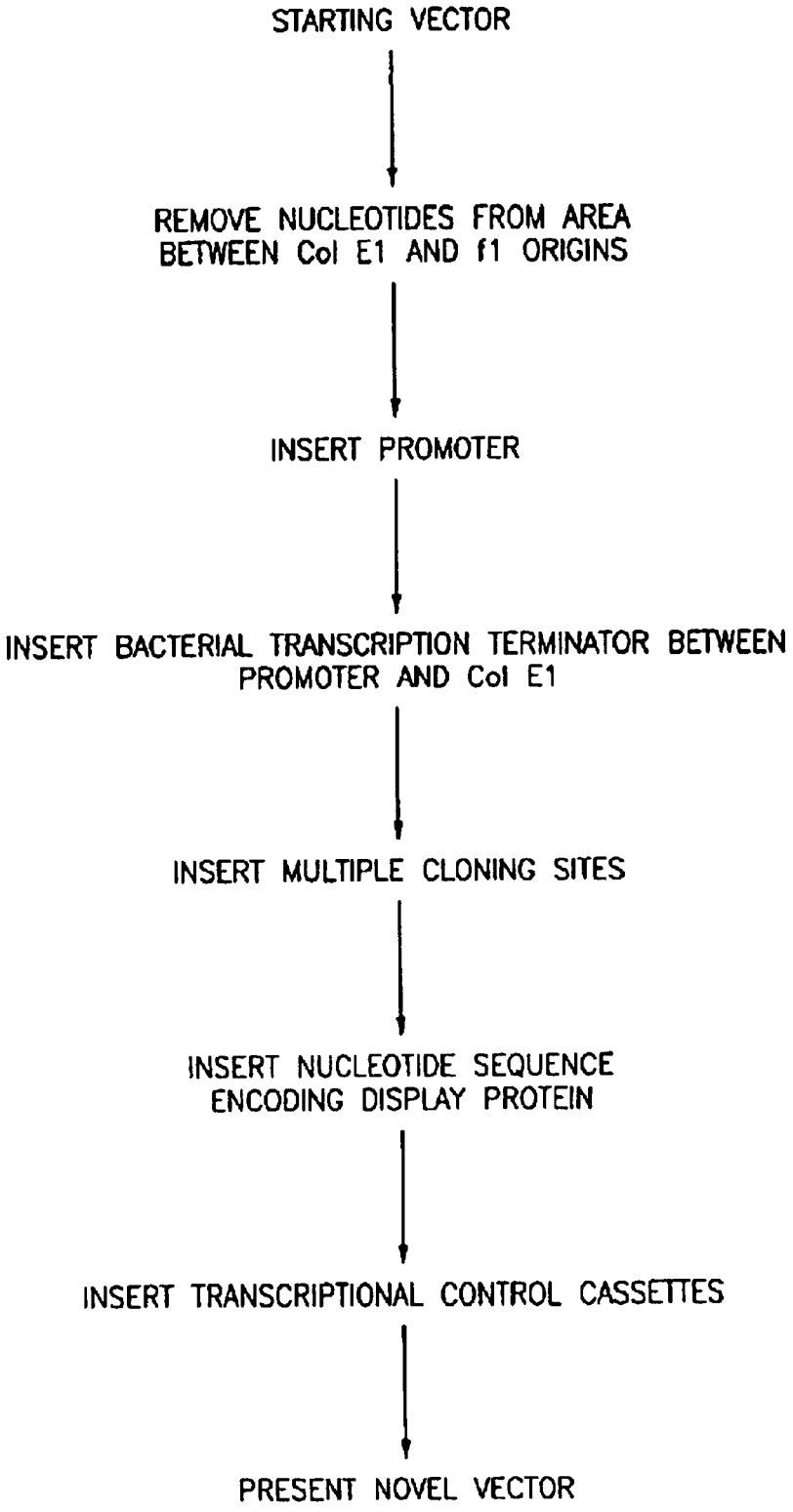
FIG. 2 is a flow chart illustrating the method of making the novel vectors described herein.

FIG. 2 is a flow-chart showing one embodiment of the steps involved in converting a starting vector into one of the present novel vectors. Those skilled in the art will readily envision other schemes for preparing the present vectors. Accordingly, the present disclosure is not limited to the sequence of steps shown in FIG. 2.

In the first step, the starting vector is digested with restriction enzymes to remove a substantial portion of the vector between the ColE1 origin and the f1 origin of replication. Typically, the portion to be removed from the starting vector includes multiple cloning sites. Depending on the particular restriction sites present in the starting vector, suitable methods for digesting the starting vector are known to and readily selected by those skilled in the art.

Next, a promoter is inserted downstream of the ColE1 origin of the digested starting vector. Any promoter recognized by a host cell can be employed. Suitable promoters include, but are not limited to, ara, lac and trc promoters. The promoter drives expression of other sequences inserted into the vector, such as, for example expression of polypeptides. In particularly useful embodiments, a promoter sequence generated from the starting vector is employed as the promoter inserted downstream of the ColE1 origin as described in more detail below.

In the next step, a bacterial transcription terminator is inserted downstream of the ColE1 origin, and upstream of the promoter. Any terminator recognized by a host cell can be employed. Suitable terminators include, but are not limited to, the $t_{HP}$ terminator, the bgIG terminator, and the crp terminator. It should be noted that bioinformatics analysis has allowed the identification of over 100 rho-independent transcription terminators in the E. coli genome, all of which should be suitable for this purpose (Ermolaeva, et al, J. Mol Biol 301:27–33 (2000)).

In the next step, multiple restriction sites are inserted downstream of the promoter. The restriction site can be any known restriction site. Suitable restriction sites for insertion include, but are not limited to Nhe I, Hind III, Nco I, Xma I, Bgl II, Bst I, Pvu I, etc. The number of restriction sites inserted is not critical, provided a sufficient number of restriction sites are inserted to allow completion of the balance of the steps needed to create the present novel vectors. Thus as few as 2 to as many as 10 or more restriction sites can be inserted in this step. It should be understood that if one or more of the restriction sites selected for insertion is present in the starting vector, it may be desirable to remove or disable the native restriction site to avoid unwanted digestion during further processing. The restriction site can be inserted using any technique known to those skilled in the art. A particularly preferred combination of restriction sites inserted in this step is Not I, Sfi I, Spe I, Xho I, Xba I and EcoR I.

The next step involves inserting a nucleotide sequence encoding a product that enables display of a polypeptide on the surface of a phagemid particle. The product encoded can thus be considered at least a functional domain of a display protein. The display protein can be any natural or synthetic polypeptide to which a polypeptide to be displayed can be fused and which can present the polypeptide to be displayed for screening processes. Suitable display polypeptides include proteins that can be incorporated into the coat of a phage particle. As those skilled in the art will appreciate, filamentous bacteriophage consist of a circular, single-stranded DNA molecule a surrounded by a cylinder of coat proteins. There are about 2,700 molecules of the major coat protein pVIII that encapsidate the phage. At one end of the phage particle, there are approximately five copies each of gene III and VI proteins (pIII and pVI) that are involved in host-cell binding and in the termination of the assembly process. The other end contains five copies each of pVII and pIX that are required for the initiation of assembly and for maintenance of virion stability. A nucleotide sequence encoding any of these coat proteins can be employed in making the novel vectors herein. Particularly preferred are nucleotide sequences encoding at least a functional domain of pIII. The nucleotide sequence encoding at least a functional domain of pill can be natural or synthetic. The nucleotide sequence inserted can encode a truncated pIII provided the display function of the protein is maintained. An example of a synthetic or artificial coat protein useful herein is that disclosed in Weiss et al., Mol Biol., 300(1), 213–219 (2000), the disclosure of which is incorporated herein by reference.

In the next step, two transcriptional control cassettes are inserted, an upstream transcriptional control cassette and a downstream transcriptional control cassette. Each of the transcriptional control cassettes include a ribosomal binding site, a leader sequence and a cloning site for receiving a gene encoding a polypeptide to be expressed. Any known ribosomal binding site (RBS) and leader sequence recognized by the host cell can be employed. Preferably, the RBS and leader sequence employed is optimized for expression in E. coli. The cloning site is a region of the nucleic acid between two restriction sites, typically with a nonessential region of nucleotide sequence (commonly referred to as a "stuffer" sequence) positioned therebetween. Alternatively, the stuffer sequence may contain a non-essential region and a portion of an antibody constant domain. Suitable stuffer sequences include, for example, those shown in FIGS. 12A–G.

The downstream transcriptional control cassette is inserted adjacent to the nucleotide sequence encoding at least the functional domain of the display protein. In this manner, a fusion protein will be expressed when a gene encoding a polypeptide to be displayed is inserted at the cloning site of the downstream transcriptional control cassette. As those skilled in the art will appreciate, a suppressible stop codon could be positioned between the gene encoding the polypeptide to be displayed and the nucleotide sequence encoding at least a functional domain of the display protein such that fusion display is obtained in a suppressing host (as long as the gene is inserted in-frame) and a secreted protein without the display protein is obtained in a non-suppressing host.

The upstream transcriptional control cassette is inserted upstream of the downstream transcriptional control cassette. The upstream transcriptional control cassette provides a second cloning region for receiving a second gene encoding a polypeptide that can dimerize with the polypeptide to be displayed. For example, where the vector expresses a heavy chain Fd fused to a display protein, the second gene preferably encodes an antibody light chain. As with the cloning site of the downstream transcriptional control cassette, the cloning site of the upstream transcriptional control cassette is a region of the vector between two restriction sites, typically with a stuffer positioned therebetween. It should of course be understood that where a polypeptide other than an antibody is to be displayed (such as, for example, where monomeric display of a single polypeptide or protein is intended) a second gene need not be cloned into the vector at the cloning site of the upstream transcriptional control cassette. In such cases the second cloning site can simply remain unused. As those skilled in the art will also appreciate, where a single chain antibody is encoded by the gene inserted at the cloning site of the downstream transcriptional control cassette, there is no need to insert a second gene into the vector at the cloning site of the upstream transcriptional control cassette.

Thus, the phagmid vector produced by the process illustrated in FIG. 2 will contain, after the ColE1 origin but before the f1 origin, a terminator, a promoter, a first ribosomal binding site, a first leader sequence and a first cloning region, a second ribosomal binding site, a second leader sequence and, a second cloning region for receiving a gene encoding a polypeptide to be displayed and a nucleotide sequence encoding at least a functional domain of a display protein.

The present vectors also include a selectable marker. Either an ampicillin resistant or a CAT resistant vector can be produced in accordance with the present disclosure. The ampicillin or CAT resistance can be provided by simply choosing a starting vector having the desired resistance. Alternatively, if the starting vector is ampicillin resistant to produce a CAT resistant vector, the ampicillin resistant gene is removed and replaced with the chloramphenicol transferase gene. Techniques for providing either ampicillin or CAT resistance in the present vectors will be readily apparent to those skilled in the art. Other suitable selectable markers include, but are not limited to, tetracycline or kanamycin resistance.

The vectors described herein can be transformed into a host cell using known techniques (e.g., electroporation) and amplified. The vectors described herein can also be digested and have a first gene and optionally a second gene ligated therein in accordance with this disclosure. The vector so engineered can be transformed into a host cell using known techniques and amplified or to effect expression of polypeptides and/or proteins encoded thereby to produce phage particles displaying single polypeptides or dimeric species. Those skilled in the art will readily envision other uses for the novel vectors described herein.

The following examples illustrate the present invention without limiting its scope. The steps involved in constructing the vectors described herein are discussed in detail in the Examples. Those skilled in the art possess knowledge of suitable techniques to accomplish the steps described below without the need for undue experimentation, such techniques being well known to those skilled in the art.

EXAMPLE 1

This example illustrates methods and compositions for the construction of one embodiment of a phagemid vector according to the present disclosure. The starting phagemid selected for construction was pBS II KS+ which contains an ampicillin resistant gene which results in a final vector, pAX131, which is ampicillin resistant.

Digestion of Starting Vector and Insertion of Promoter

Figure 3:
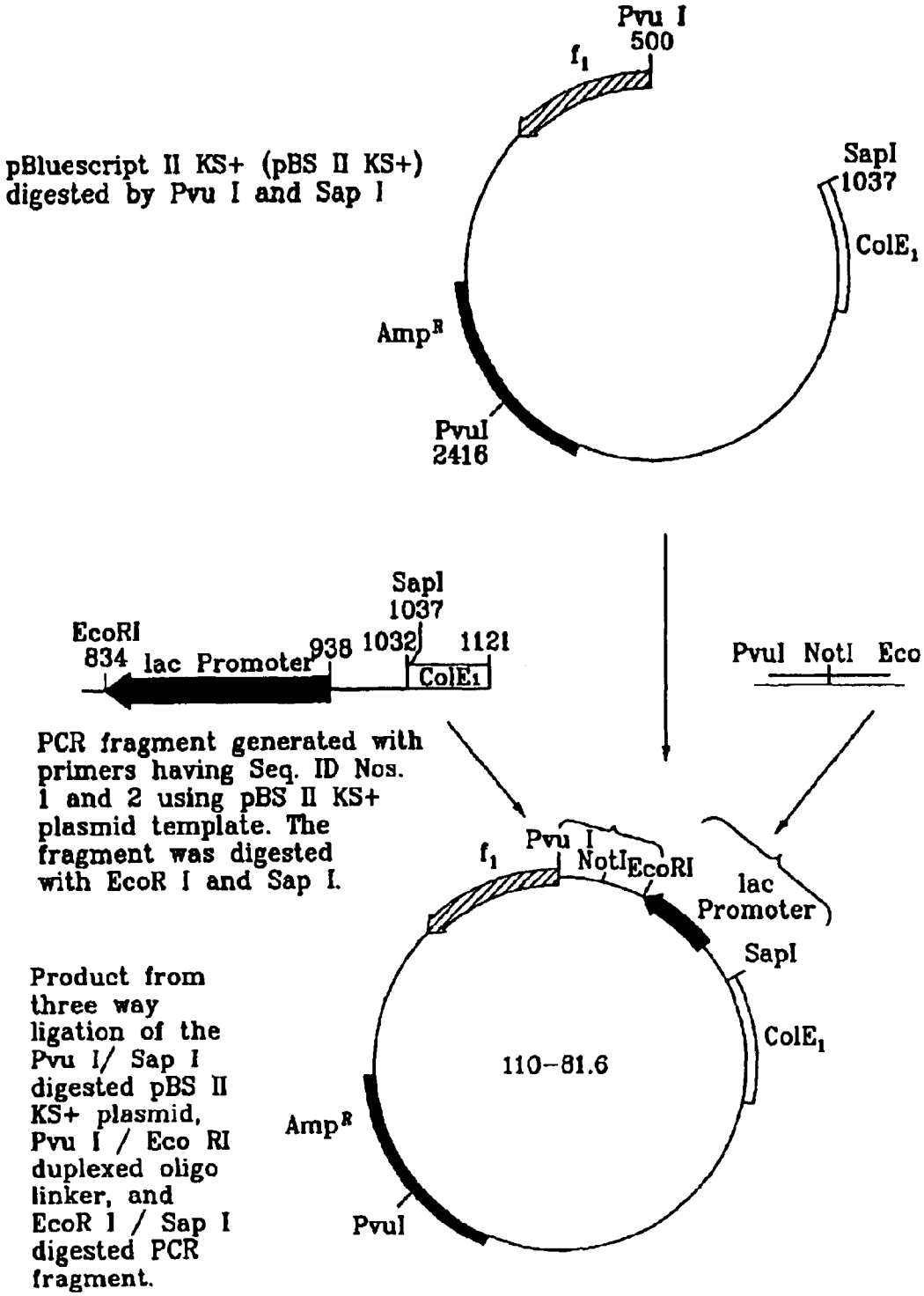
FIG. 3 schematically illustrates the digestion of the starting vector and insertion of the promoter.

The commercially available vector pBS II KS+ (Stratagene, LaJolla, Calif.) was digested with Pvu I and Sap I to generate a 2424 bp pBS II KS+ fragment which lacks the bases at positions 500 to 1037 corresponding to the multiple cloning region. The resulting fragment contains the Ampicillin resistant gene (AmpR), phage f1 origin, and the Col E1origin. (See FIG. 3.) Next, two mutagenic primers were used with the pBS II KS+ fragment in a PCR reaction followed by digestion with EcoR I and Sap I to generate a 209 bp fragment containing the lac promoter. The primers used were as follows:

5' AAC CGT ATT ACC GCC TTT GAG TG 3' (SEQ. ID. NO. 1):

and

5' CCT GAA TTC AAT TGT TAT CCG CTC ACA ATT CCA C 3' (SEQ. ID. NO. 2).

The 2424 bp fragment and the 209 bp fragment were combined in a three-way ligation reaction with two overlapping oligonucleotides which contain a Not I, EcoR I and Pvu I sites to form a first intermediate plasmid (designated p110-81.6). (See FIG. 3.) The oligonucleotides used for this reaction were:

5' CGG TAA TGC GGC CGC TAC ATG 3' (SEQ. ID. NO. 3);

and

5' AAT TCA TGT AGC GGC CGC ATT ACC GAT 3' (SEQ. ID. NO. 4).

Figure 4A:
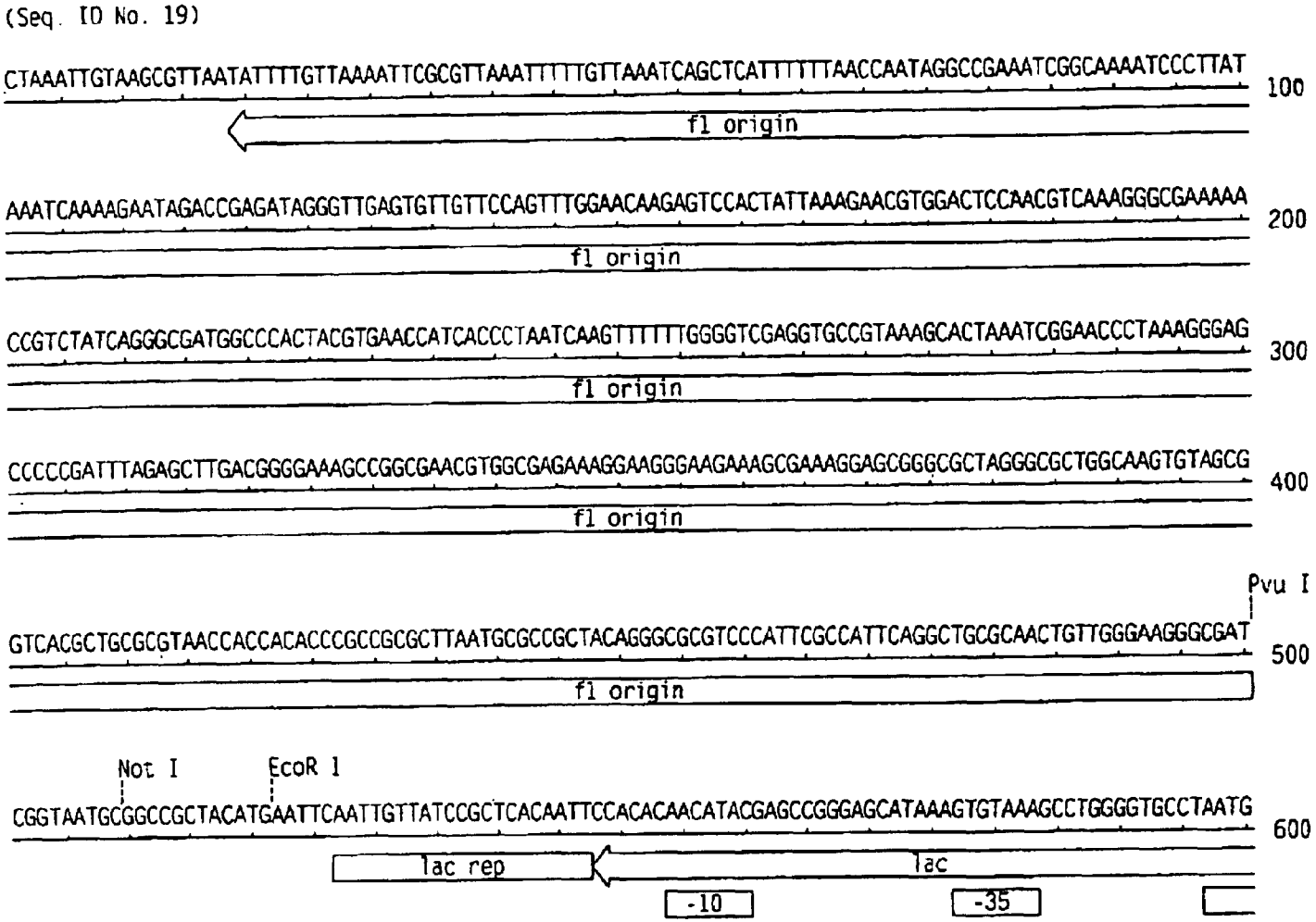
Figure 4A:
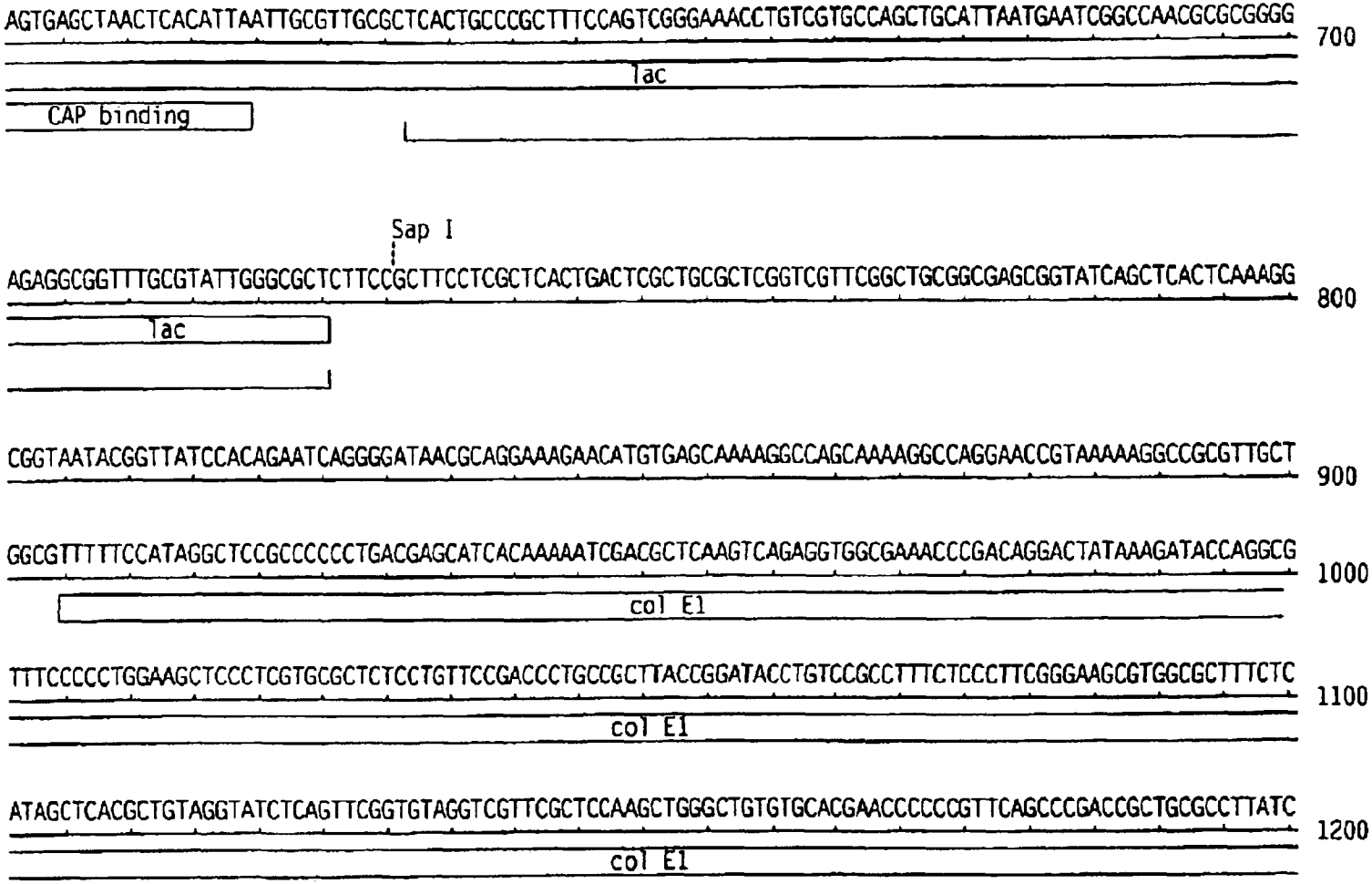
Figure 4B:
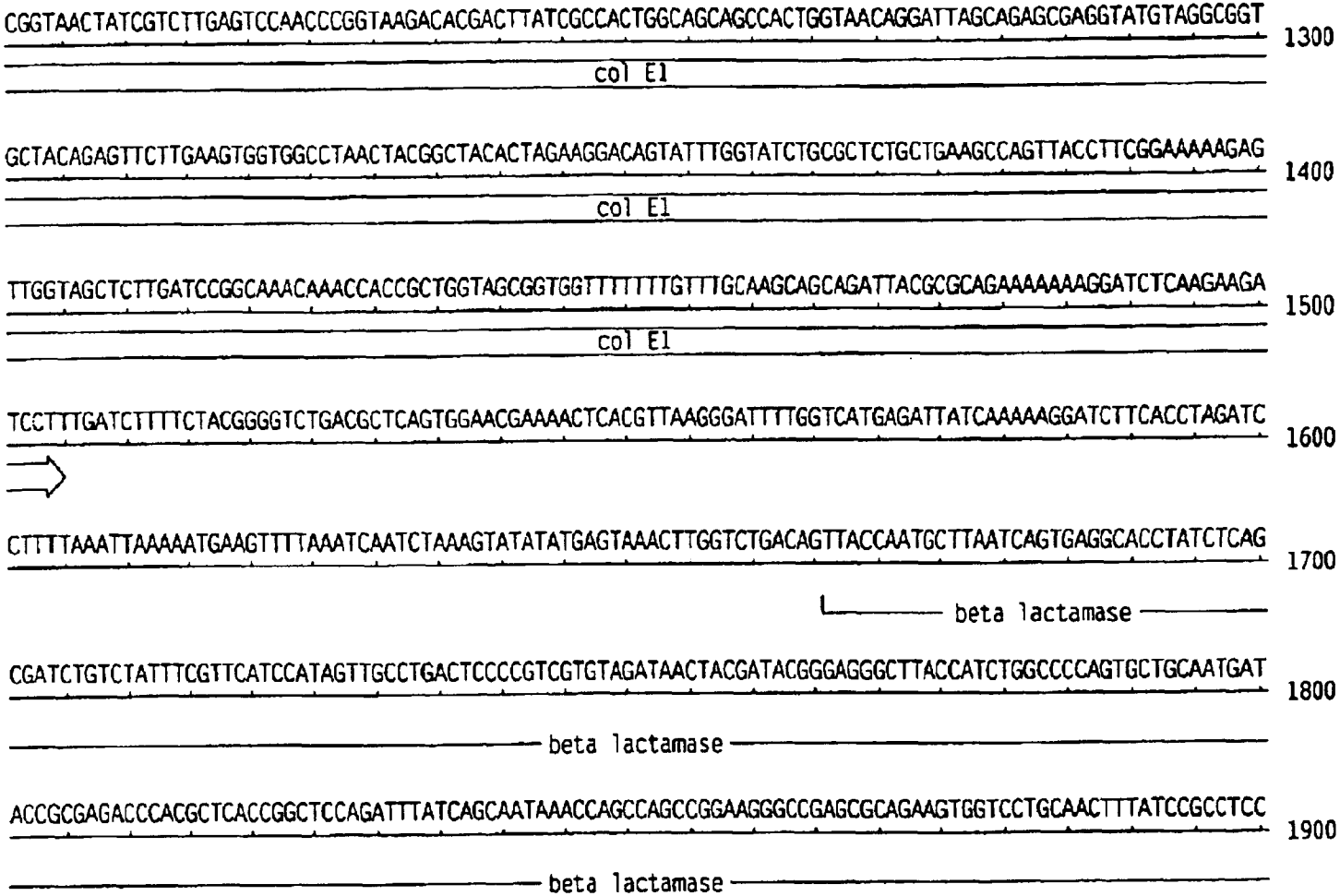

The resulting plasmid p110-81.6 was digested and sequenced in the altered region to identify a clone with the correct incorporation of the lac promoter, Pvu I, Sap I, EcoR, and Not I sites. The sequencing of p110-81.6 revealed a nucleic acid change at position 875 within the lac promoter. The published sequence of pBS II KS+ had an adenine at position 875. However, sequencing of p110-81.6 and the original pBS II KS+ revealed a guanine at position 875. The sequence (Seq. ID No. 19) of intermediate plasmid p110-81.6 is shown in FIGS. 4A–C.

Insertion of Terminator

Figure 5:
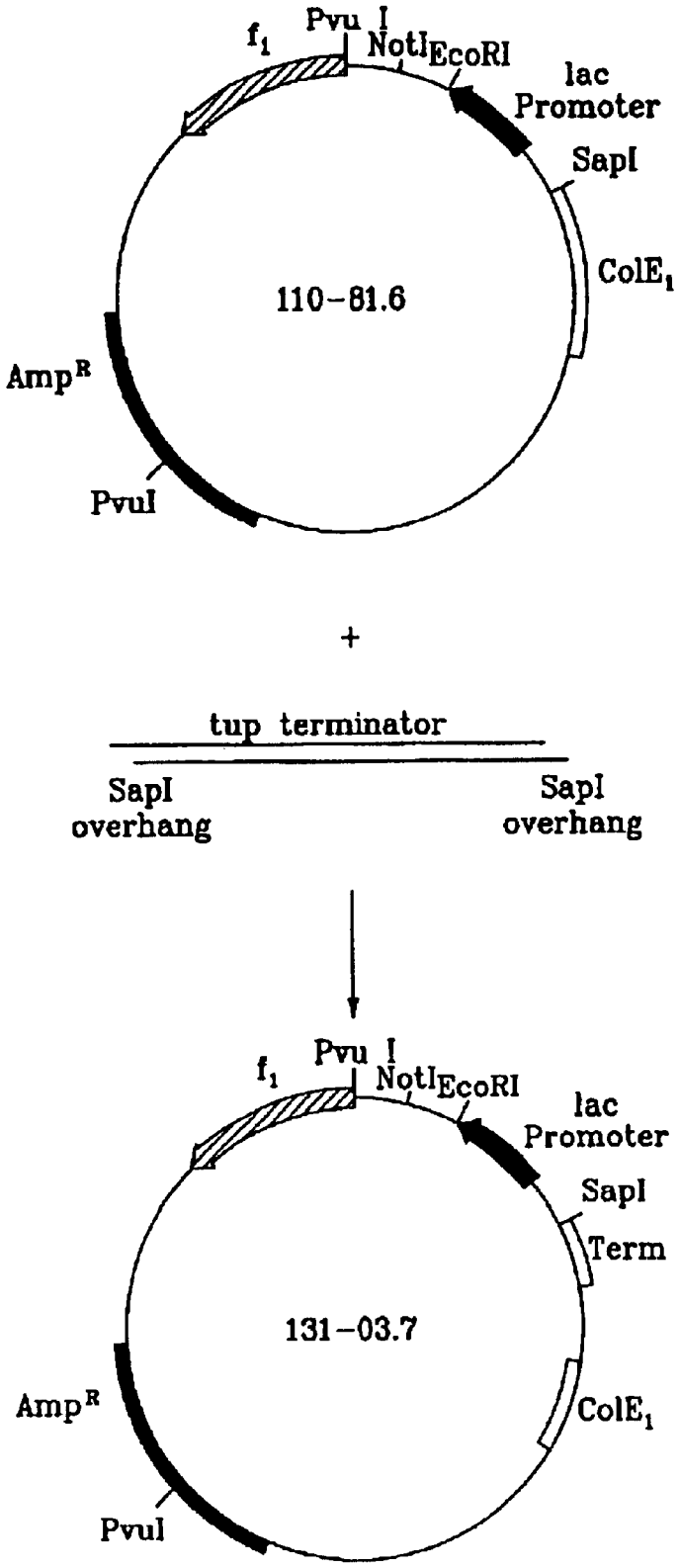
FIG. 5 schematically illustrates the insertion of the terminator.

A transcription termination sequence was inserted into the first intermediate plasmid (p110-81.6) upstream of the lac promoter at the Sap I site. (See FIG. 5.)

Plasmid 110-81.6 was digested with Sap I to create an insertion point for the oligonucleotides which contained a $t_{HP}$ terminator (Nohno et al., Molecular and General Genetics, Vol. 205, pages 260-269 (1986). The oligonucleotides used in this ligation were:

5' AGC GTA CCC GAT AAA AGC GGC TTC CTG ACA GGA GGC CGT TTT GTT TTG CAG CCC ACC T 3'; (SEQ. ID. No. 5);

and

5' GCT AGG TGG GCT GCA AAA CAA AAC GGC CTC CTG TCA GGA AGC CGC TTT TAT CGG GTA C 3' (SEQ. ID. NO. 6).

Figure 6A:
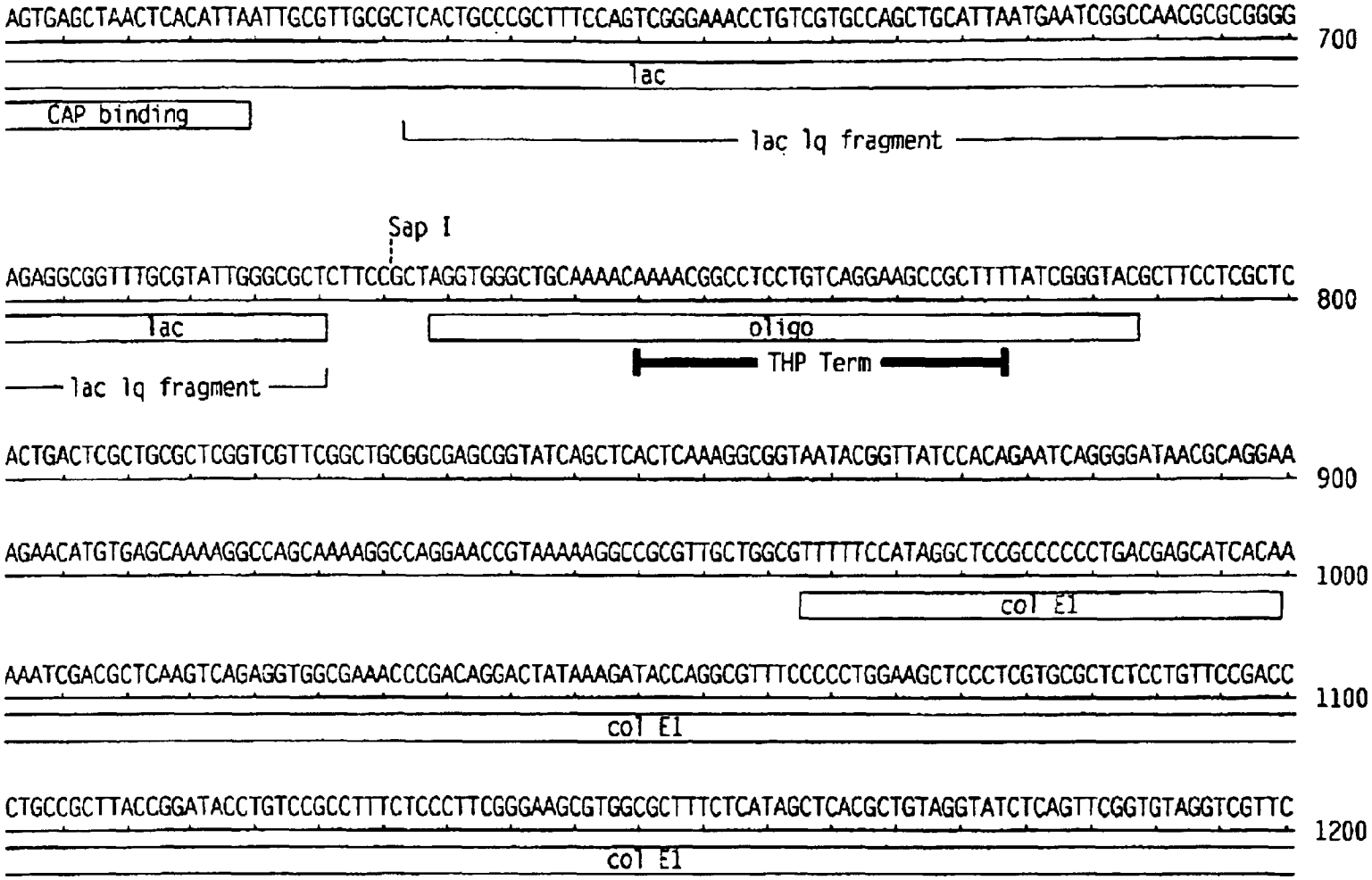
Figure 6B:
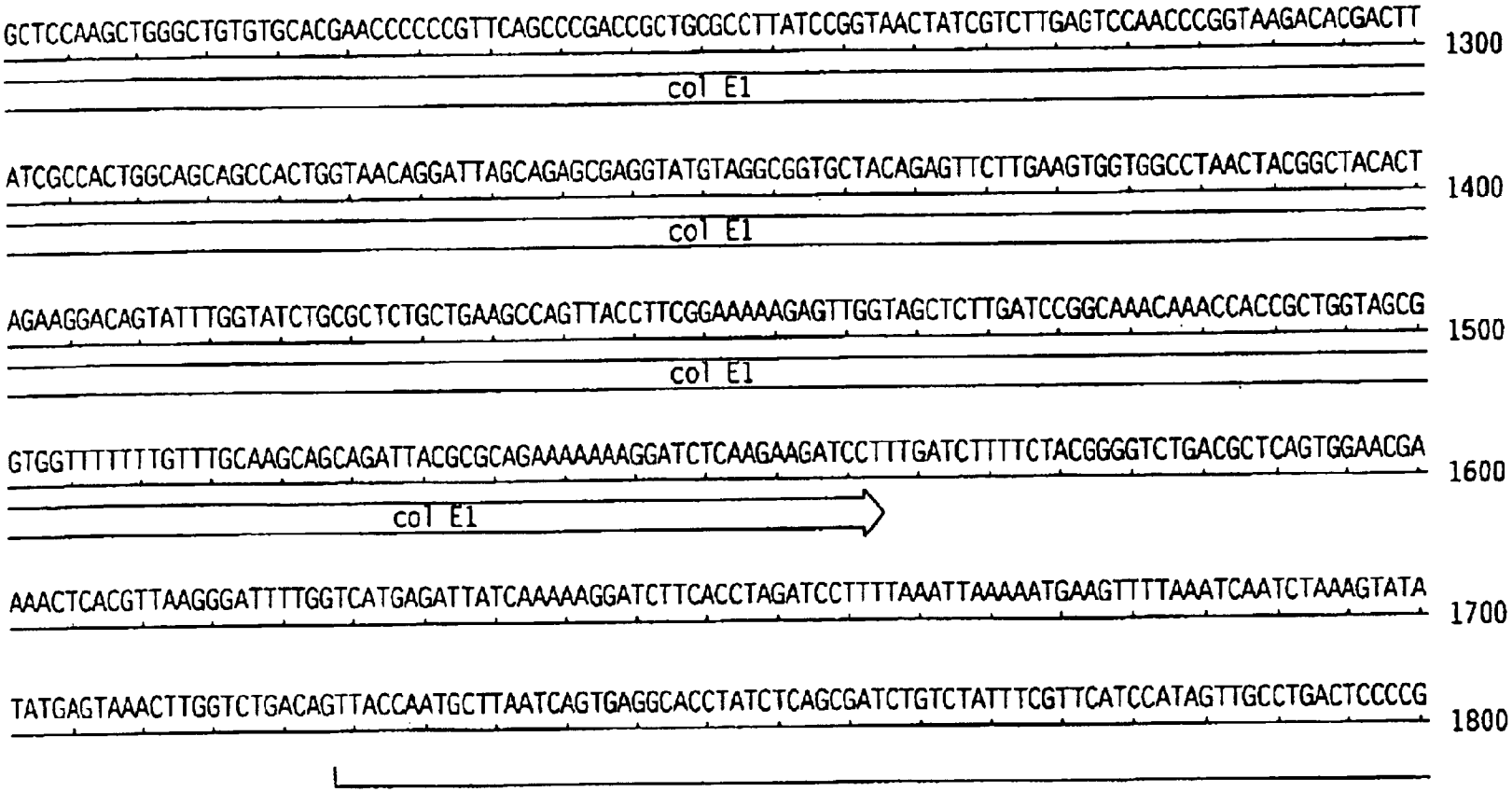

The resulting intermediate vector (designated p131-03.7) was digested and sequenced in the altered region to determine its identity. The sequence (Seq. ID No. 20) of intermediate vector p131-03.7 is shown in FIGS. 6A–C.

Insertion of Multiple Restriction Sites

Figure 7:
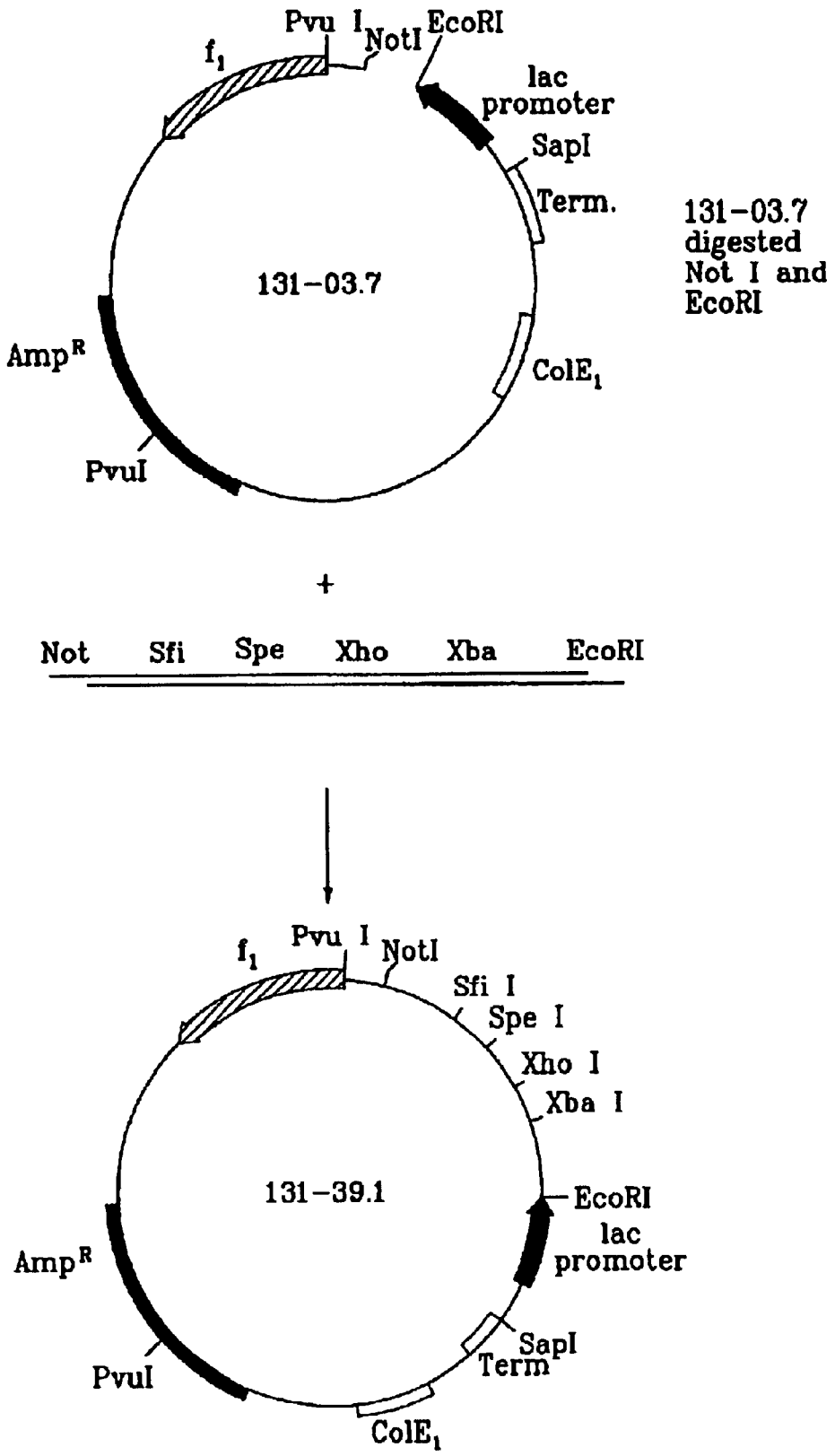
FIG. 7 schematically illustrates the insertion of multiple cloning sites.

Oligonucleotides containing the Xba I, XhoI, SpeI and Sfi sites were then inserted into intermediate plasmid p131-03.7.(See FIG. 7.)

Intermediate vector p131-03.7 was digested with EcoR I and Not I and then gel purified. Then overlapping oligonucleotides containing the Xba I, Xho I, Spe I and Sfi I sites were ligated into the p131-03.7 backbone. The oligonucleotides inserted were:

5' AAT TCA CAT CTA GAT ATC TCG AGT CAA TAC TAG TGG CCA GGC CGG CCA GC 3' (SEQ. ID. NO. 7);

and

5' GGC CGC TGG CCG GCC TGG CCA CTA GTA TTG ACT CGA GAT ATC TAG ATG TG 3' (SEQ. ID. NO. 8).

Figure 8B:
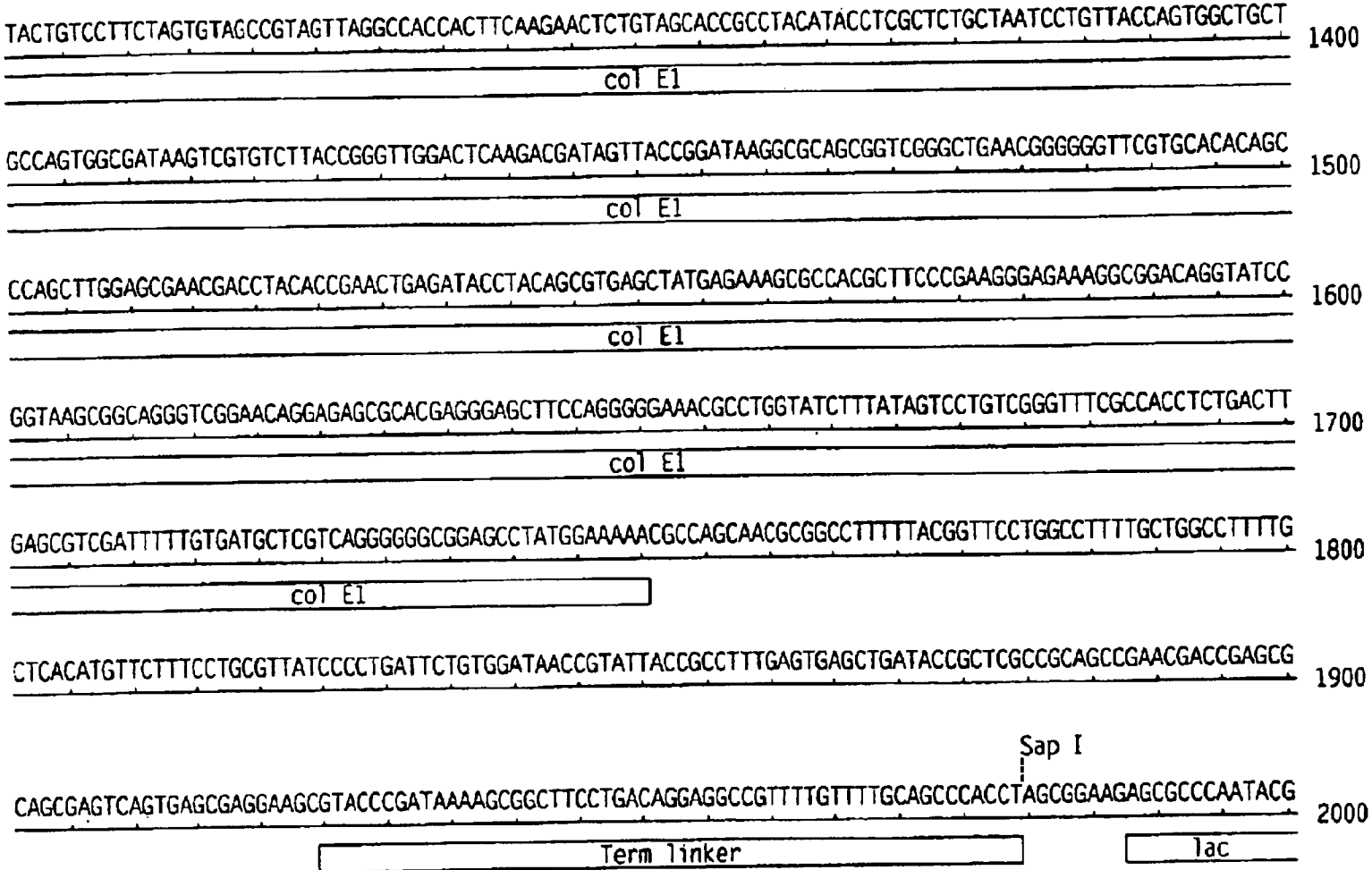
Figure 8C:
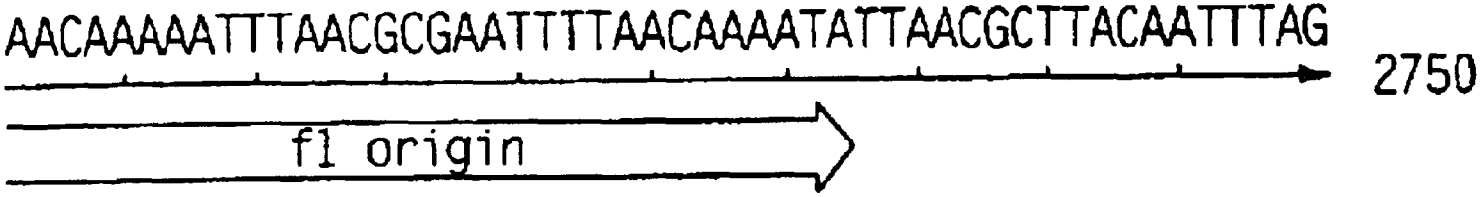

The resulting intermediate plasmid (designated p131-39.1) was sequenced and analyzed to determine its identity. The sequence (Seq. ID No. 21) of intermediate plasmid p131-39.1 is shown in FIGS. 8A–C.

Construction of Nucleotide Sequence Encoding Display Protein

Single stranded DNA from phage f1 (ATCC #15766-B2) was used as a template for the cloning of gene III. (Sec FIG. 9.)

The primers used were:

5' AGT GGC CAG GCC GGC CTT GAA ACT GTT GAA AGT TGT TTA GCA AA 3' (SEQ. ID. NO. 9)

which contains the Sfi I site, bases to maintain the coding frame and a portion of gene III; and 5 TCT GCG GCC GCT TAG CTA GCT TAA GAC TCT TTA TTA CGC AGT ATG TTA GCA 3' (SEQ. ID. NO. 10);

which contains the end of gene III in which an internal ribosome binding site ordinarily used for the next downstream gene has been removed by changing a silent third base position in the corresponding codon. This oligonucleotide also contains a stop codon, Nhe I site for potential use in removal of the fusion, a second stop codon for use with the fusion, and the Not I site for cloning. The PCR fragment was digested with Sfi I and Not I and inserted into p131-39.1 digested with Sfi I and Not I to create intermediate vector p131-44.2. The integrity of the gene III region and flanking sequences was confirmed by sequence analysis.

Creation of the Upstream Transcriptional Control Cassette

Plasmid 131-39.1 was utilized as a shuttle vector for cloning the oligonucleotides containing the ompA signal peptide coding sequence. The upstream transcriptional control cassette was generated within intermediate plasmid 131-39.1 by inserting a pair of oligonucleotides which contain EcoR I, the ompA signal peptide leader, followed by a Sac I site, a small stuffer region, and a ribosome binding site. (See FIG. 9.) The oligonucleotides used were:

Eco Xba:

5' AAT TCA AGG AGT TAA TTA TGA AAA AAA CCG CGA TTG CGA TTG CGG TGG CGC TGG CGG GCT TTG CGA CCG TGG CCC AGG CGG CCG AGC TCA TCT T 3' (SEQ. ID. NO. 11);

and

Xba Eco:

5' CTA GAA GAT GAG CTC GGC CGC CTG GGC CAC GGT CGC AAA GCC CGC CAG CGC CAC CGC AAT CGC AAT CGC GGT TTT TTT CAT AAT TAA CTC CTT G 3' (SEQ. ID. NO. 12).

The RBS and leader sequences included in the upstream transcriptional control cassette are optimized for use in E. coli. These novel sequences are:

5' AAG GAG 3' (Seq. ID No.13)

for the RBS; and

5' ATG AAA AAA ACC GCG ATT GCG ATT GCG GTG GCG CTG GCG GGC TTT GCG ACC GTG GCC CAG GCG GCC 3' (Seq. ID No. 14)

for the ompA leader. The resulting plasmid was sequenced to confirm the identity of the insert and digested at the EcoRI and XbaI sites to generate a 94 bp fragment which is the upstream transcriptional control cassette.

Creation of the Downstream Transcriptional Control Cassette

Intermediate plasmid 131-39.1 was utilized as a shuttle vector for cloning the oligonucleotides containing the pelB signal peptide coding sequence. The downstream transcriptional control cassette was generated within intermediate plasmid 131-39.1 by inserting a pair of oligonucleotides containing the pelB signal peptide, Xba I, site, and a ribosome binding site. The oligonucleotides used were:

XbaXho:

5' CTA GAT ATA ATT AAG GAG ATA AAT ATG AAA TAT CTG CTG CCG ACC GCG GCG GCG GGC CTG CTG CTG CTG GCG GCG CAG CCG GCG ATG GCGC 3' (SEQ. ID. NO. 15);

and

XhoXba:

5' TCG AGC GCC ATC GCC GGC TGC GCC GCC AGC AGC AGC AGG CCC GCC GCC GCG GTC GGC AGC AGA TAT

TTC ATA TTT ATC TCC TTA ATT ATA T 3' (SEQ. ID. NO. 16).

The novel pelB leader sequence was optimized for use in E. coli and had the sequence 5' TAT GAA ATA TCT GCT GCC GAC CGC GGC GGC GGG CCT GCT GCT GCT GGC GGC GCA GCC GGC GAT GGC G 3' (Seq. ID No. 17).

The resulting plasmid was sequenced to confirm the identity of the insert and digested at the Xbal and XhoI sites to generate a 91 bp fragment which is the downstream transcriptional control cassette.

Construction of pAx131 Vector

Figure 9:
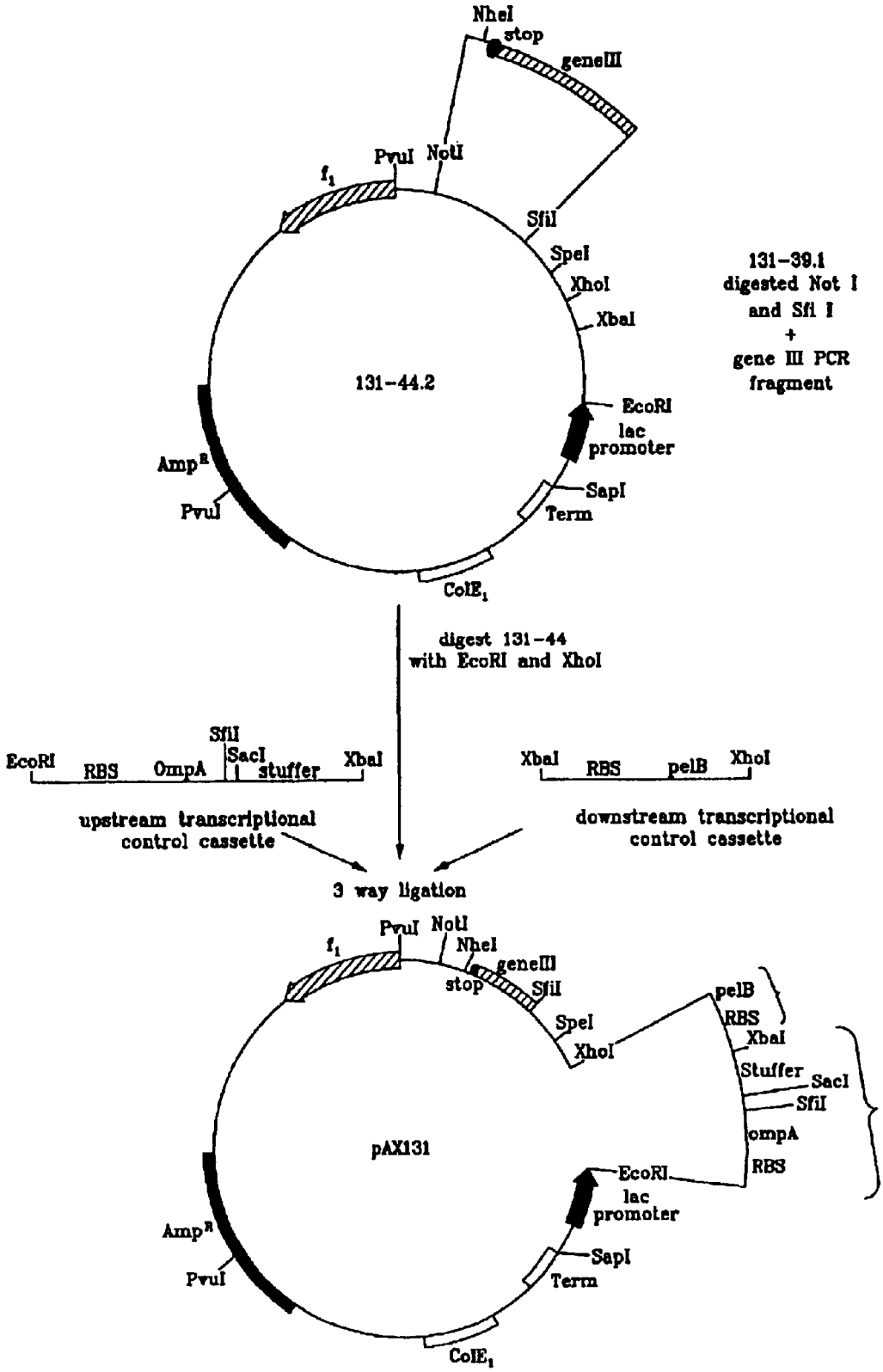
FIG. 9 schematically illustrates the insertion of the nucleotide sequence encoding the display protein and the two transcriptional control cassettes.
Figure 10:
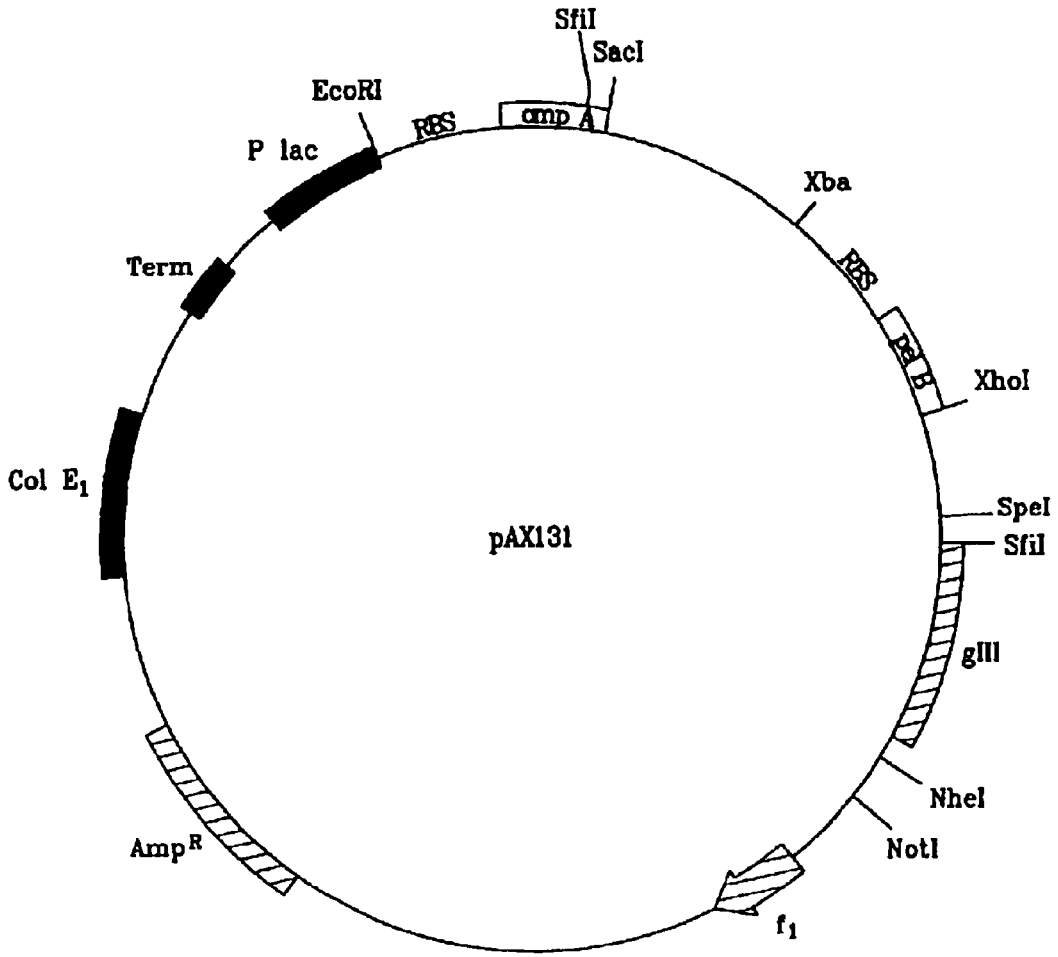
FIG. 10 is a map of plasmid pAX131.
Figure 11A:
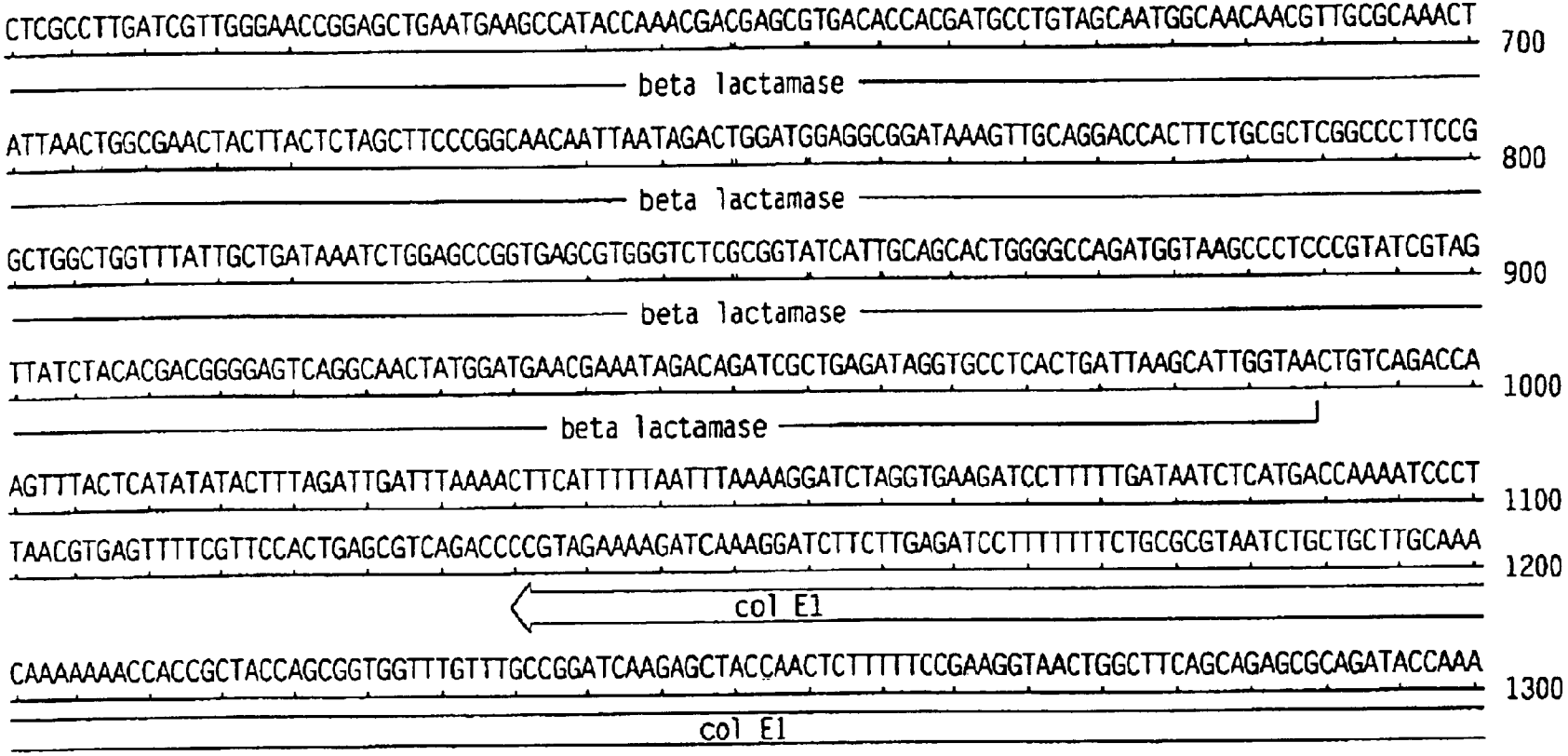
FIGS. 11A–D show the nucleic acid sequence (Seq. ID No. 18) of plasmid pAX131, including the domains corresponding to particular genes.
Figure 11B:
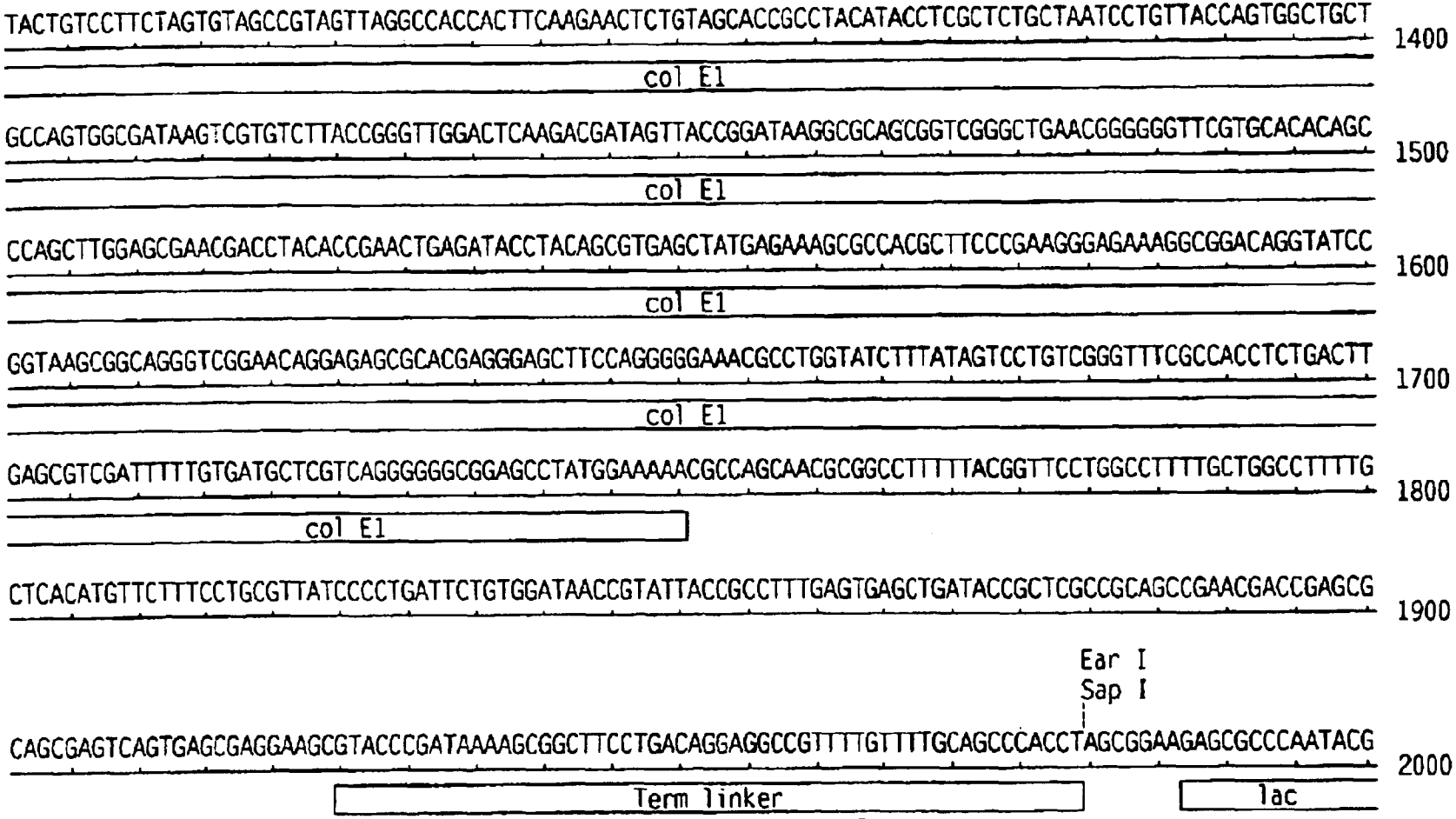
Figure 11B:
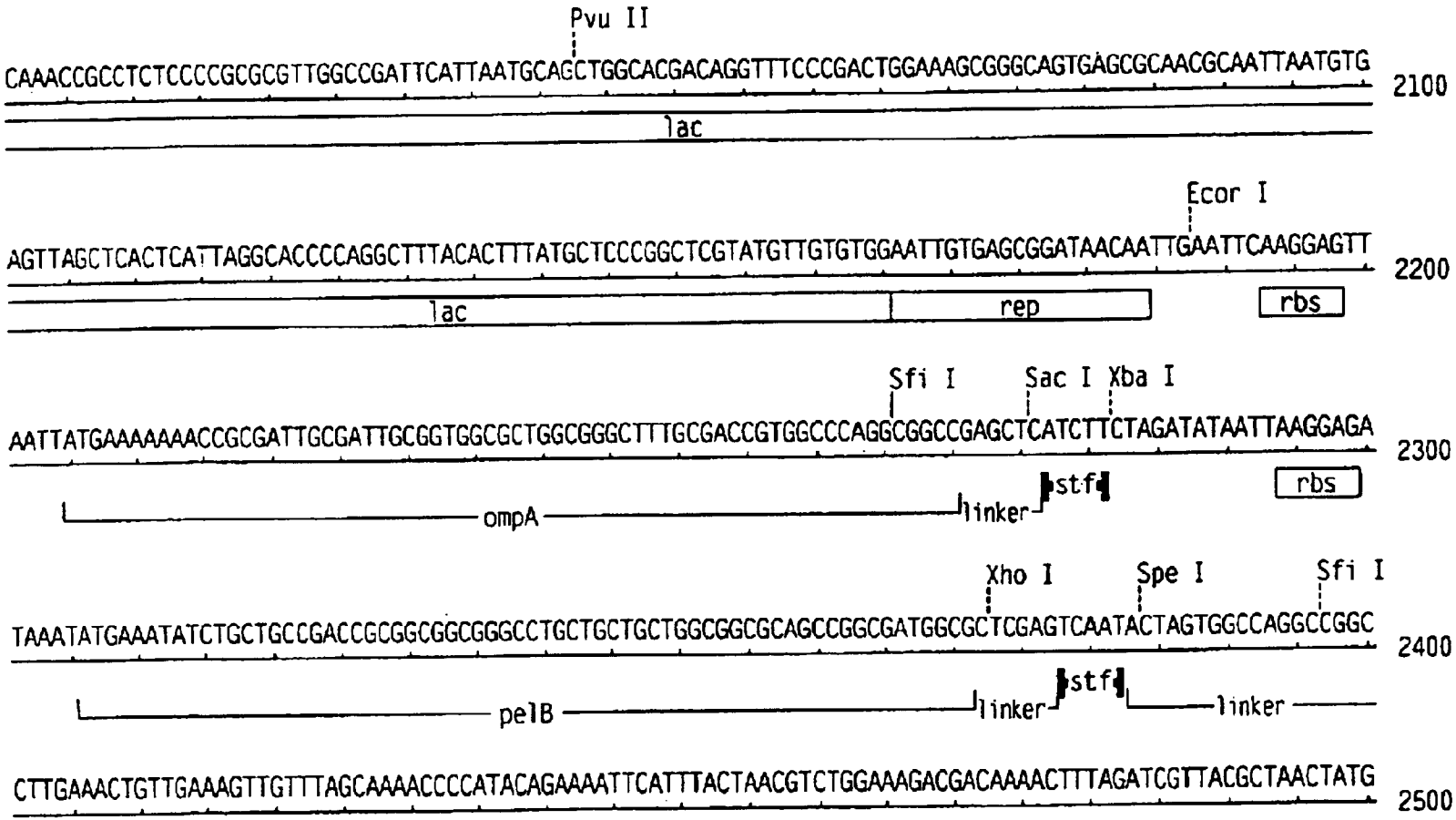
Figure 11C:
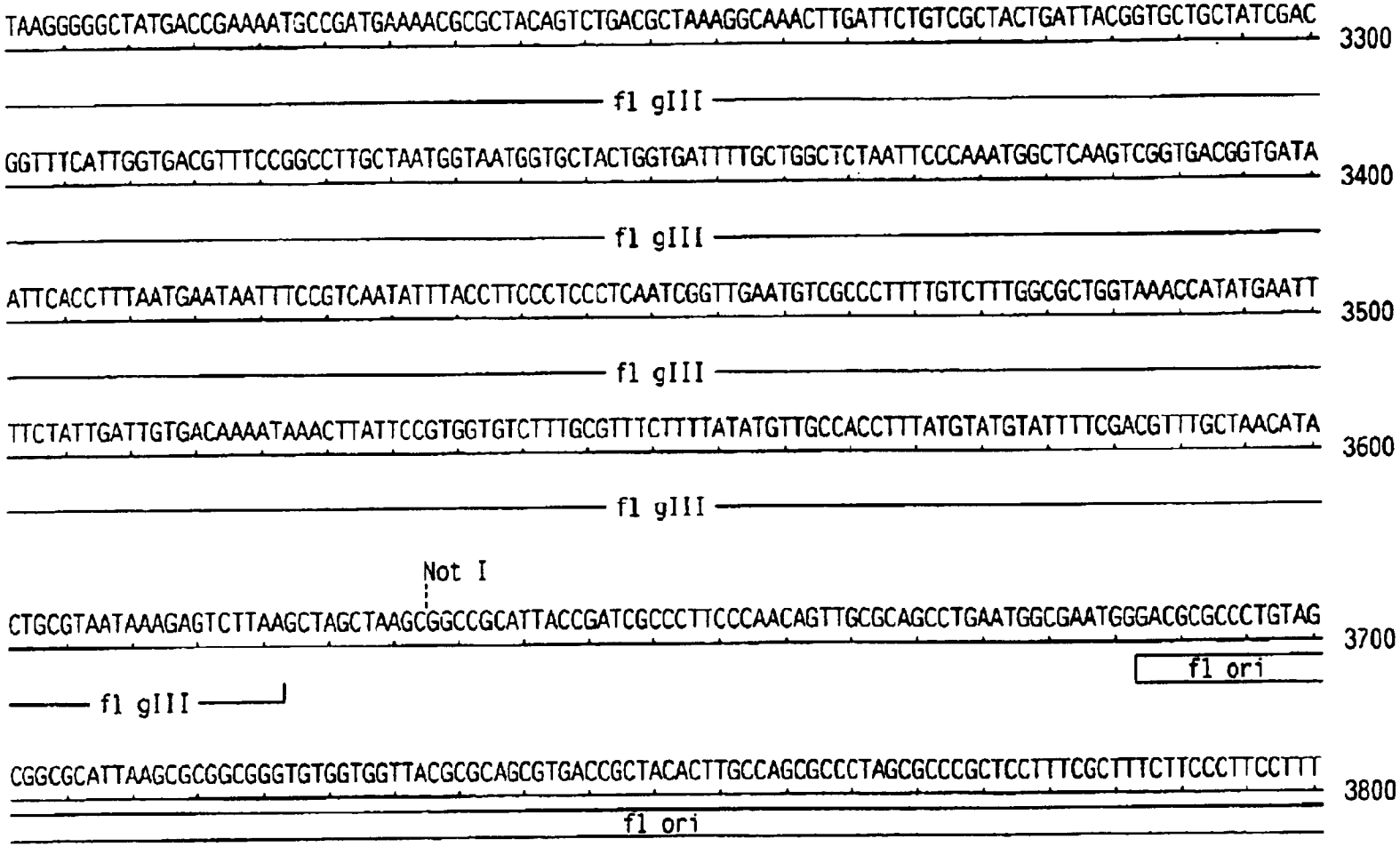
Figure 11D:
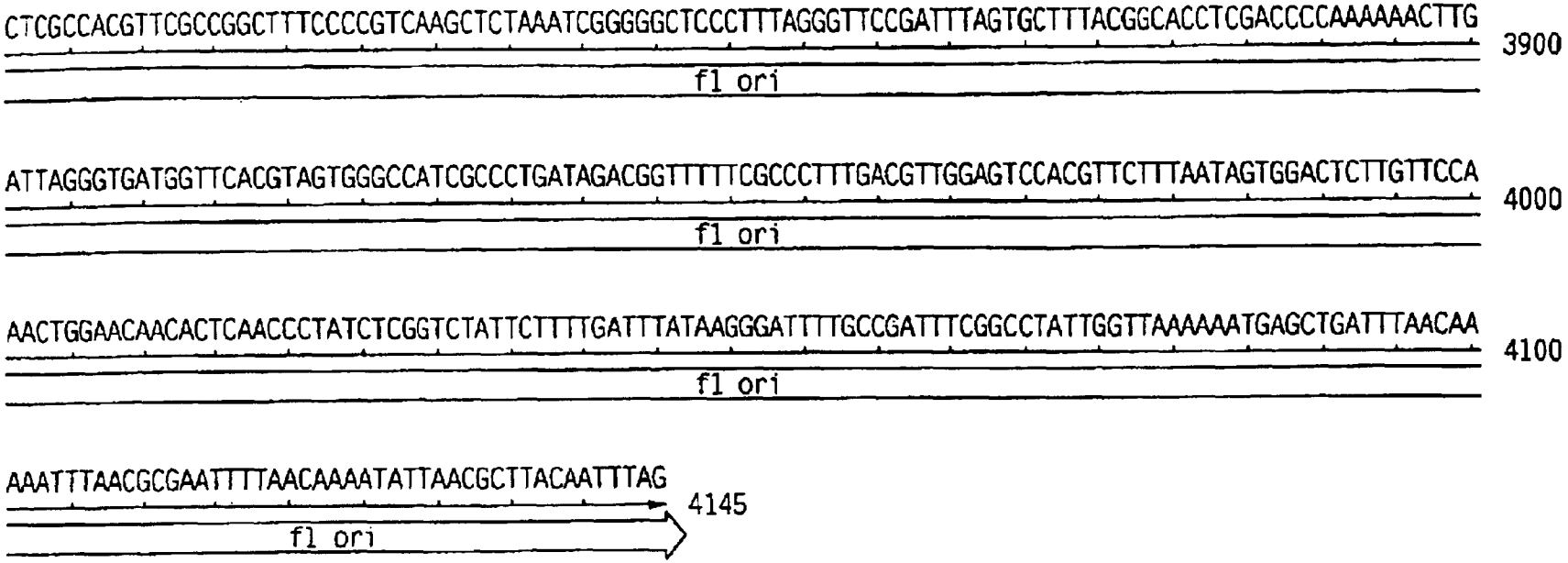
Figure 12A:
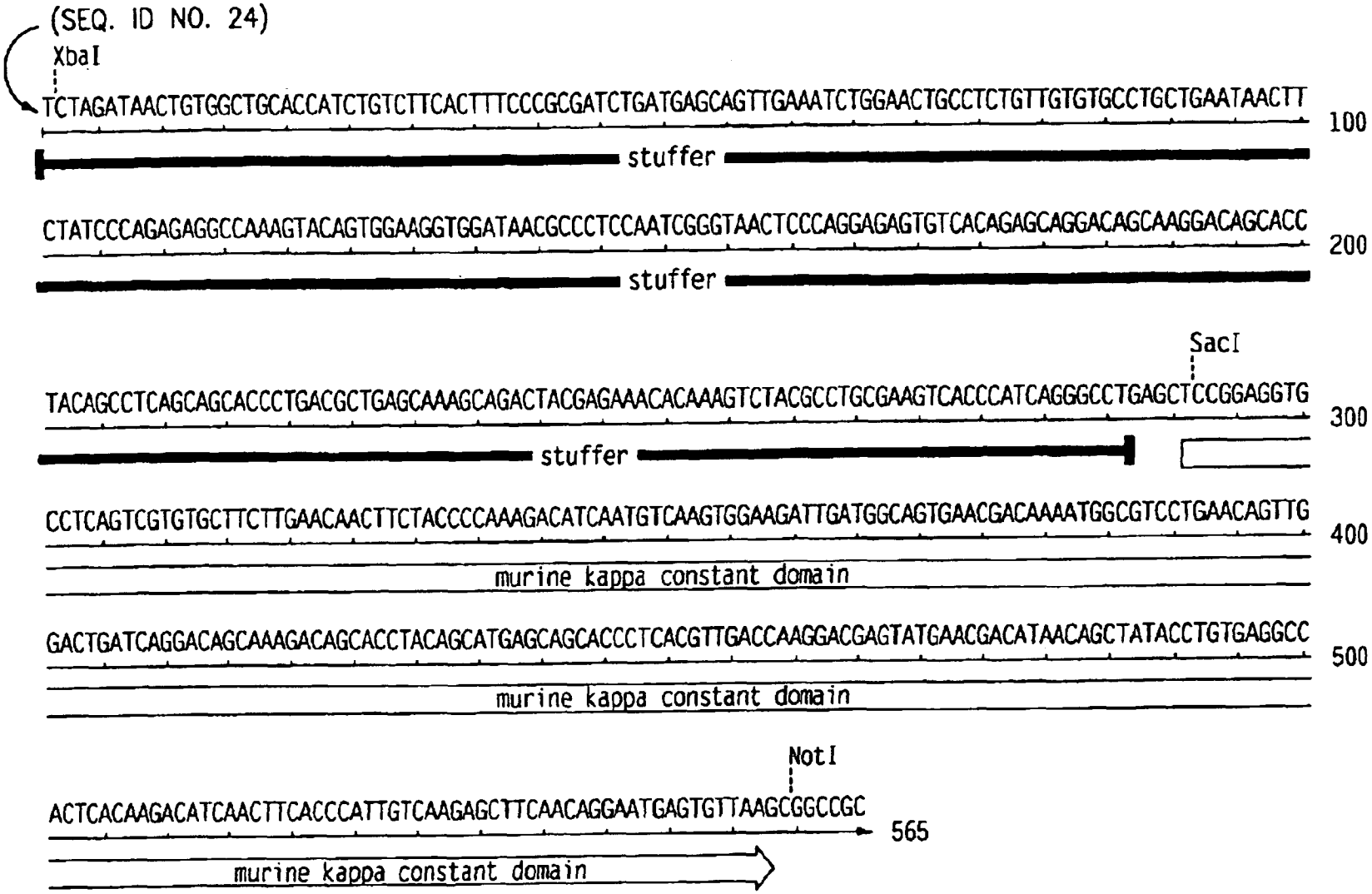
Figure 12B:
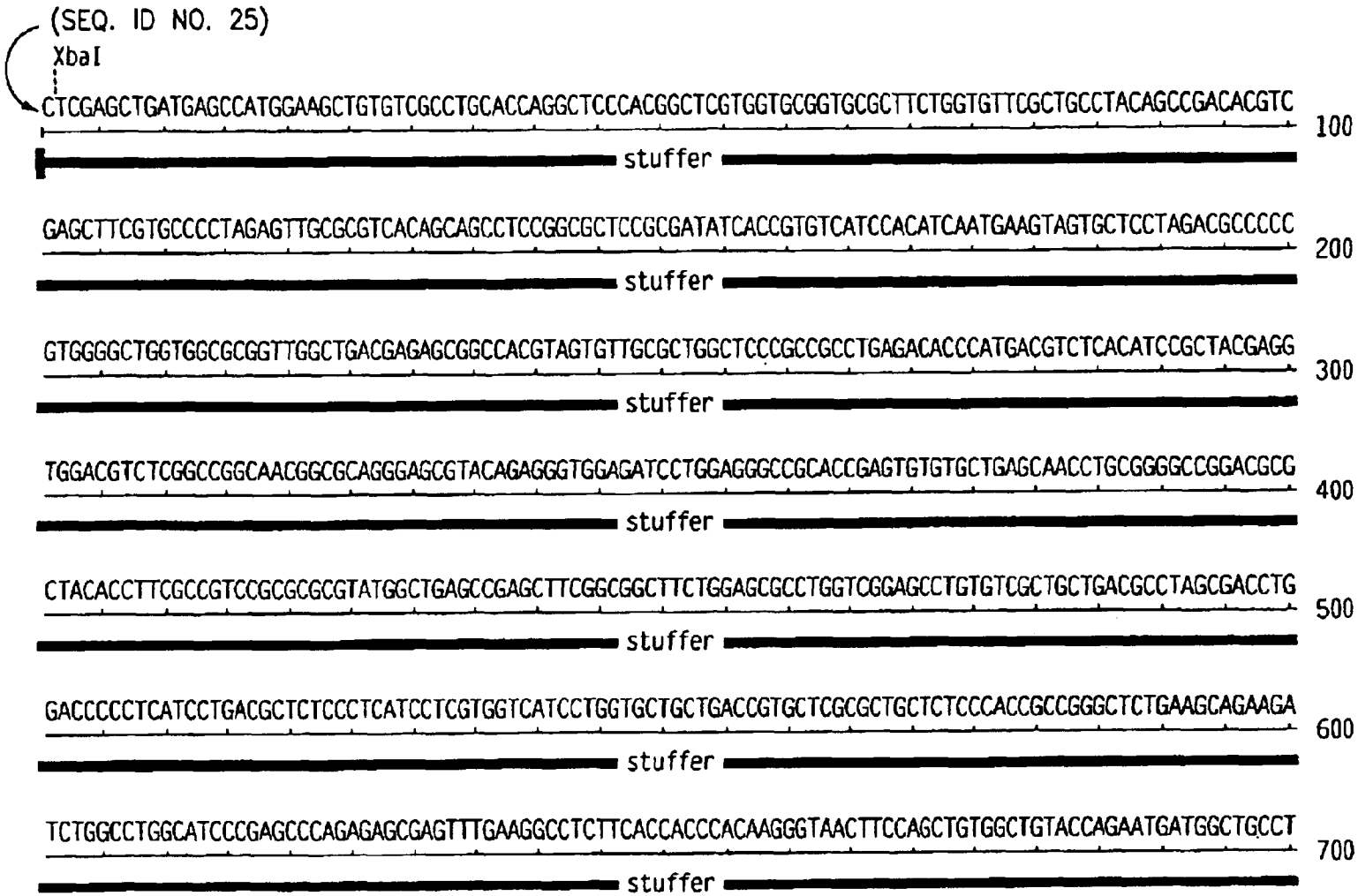
Figure 12B:
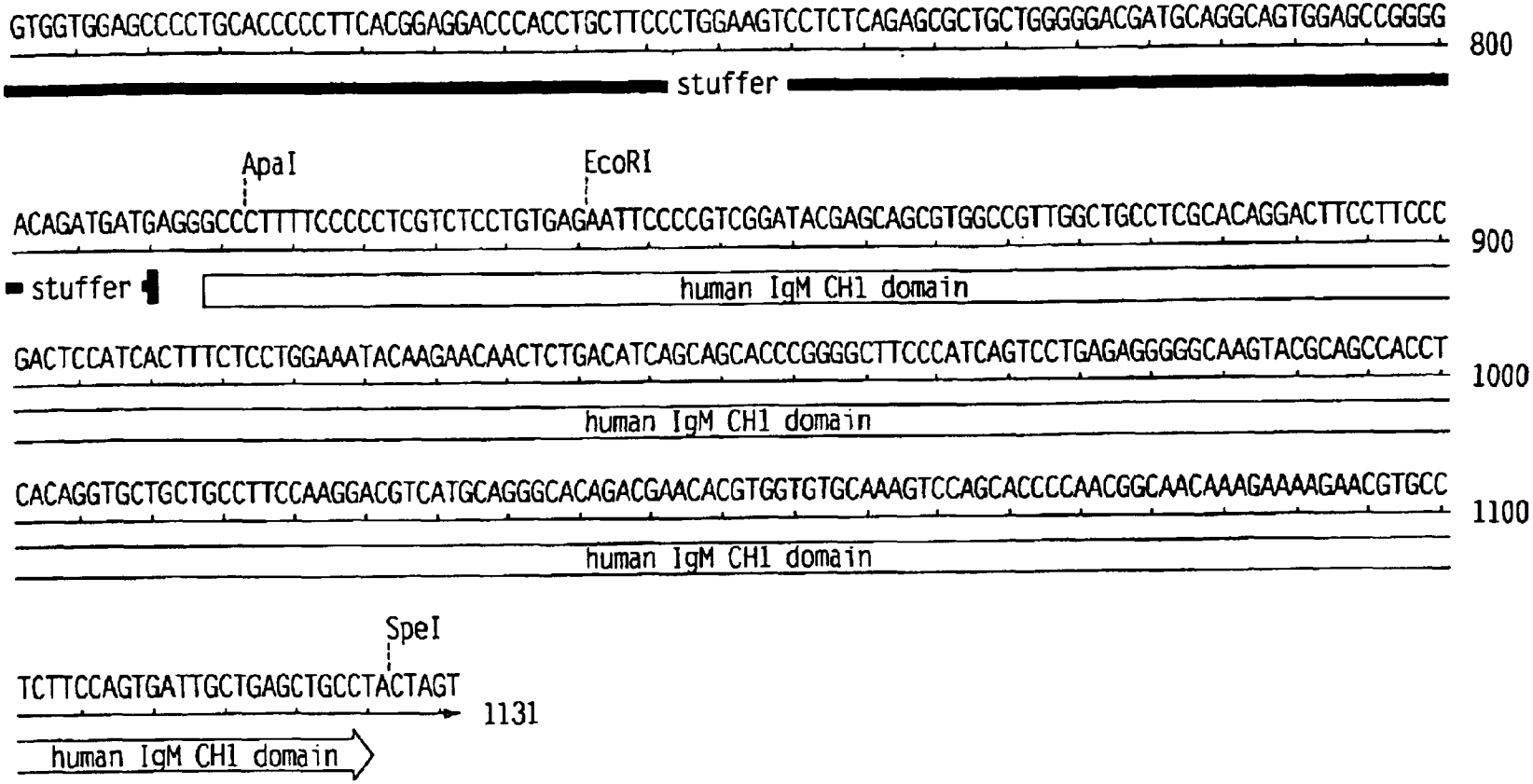
Figure 12C:
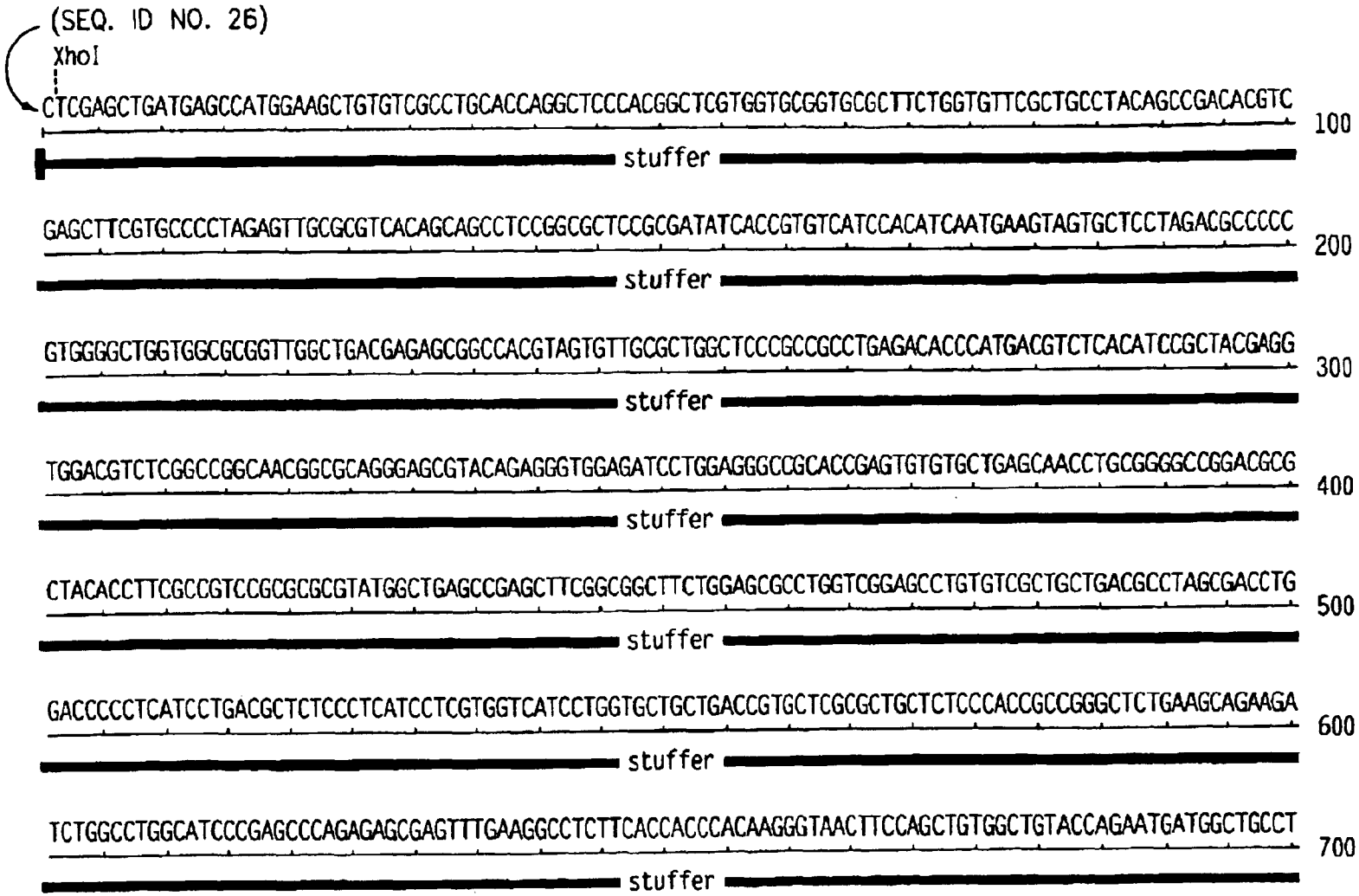
Figure 12C:
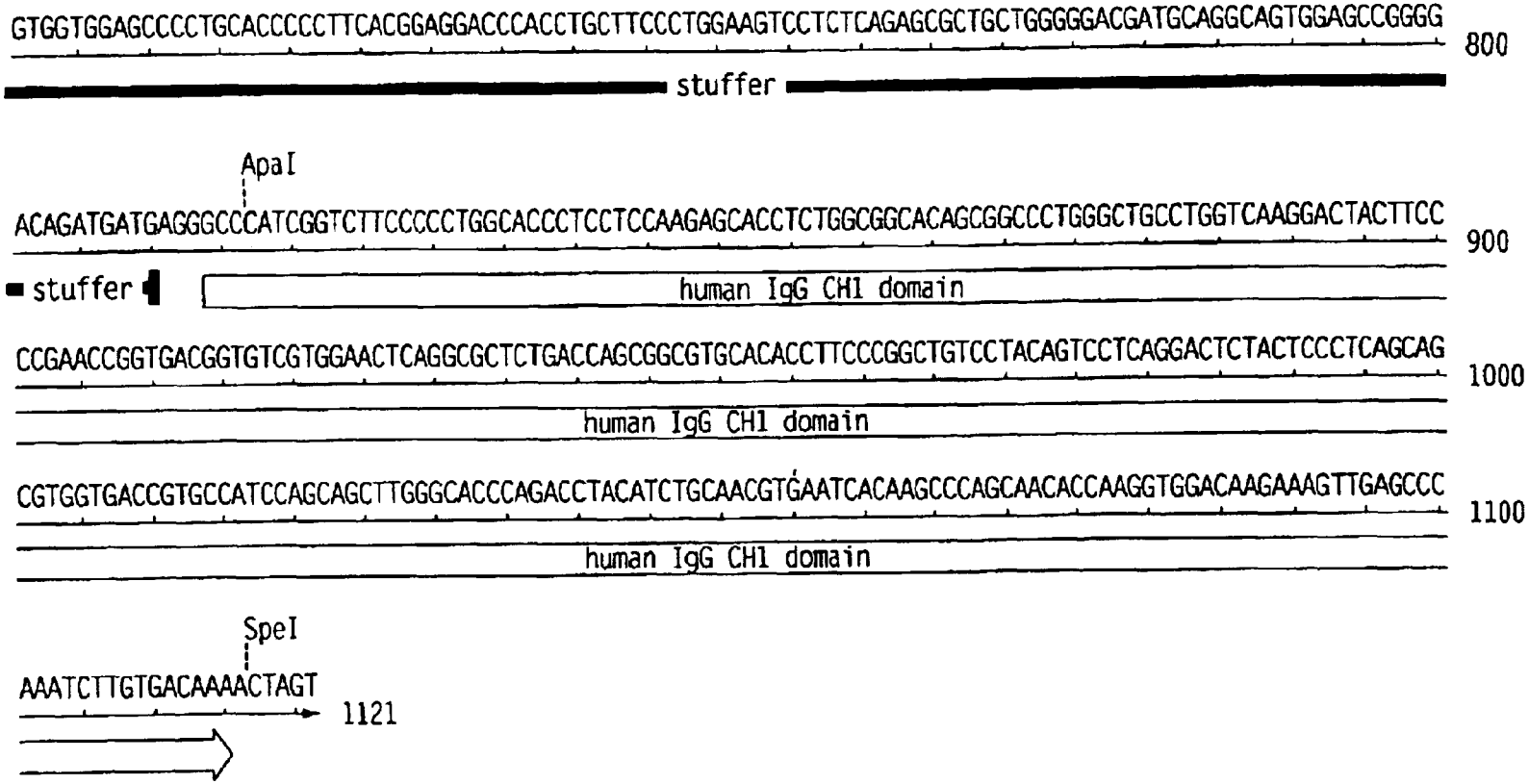
Figure 12D:
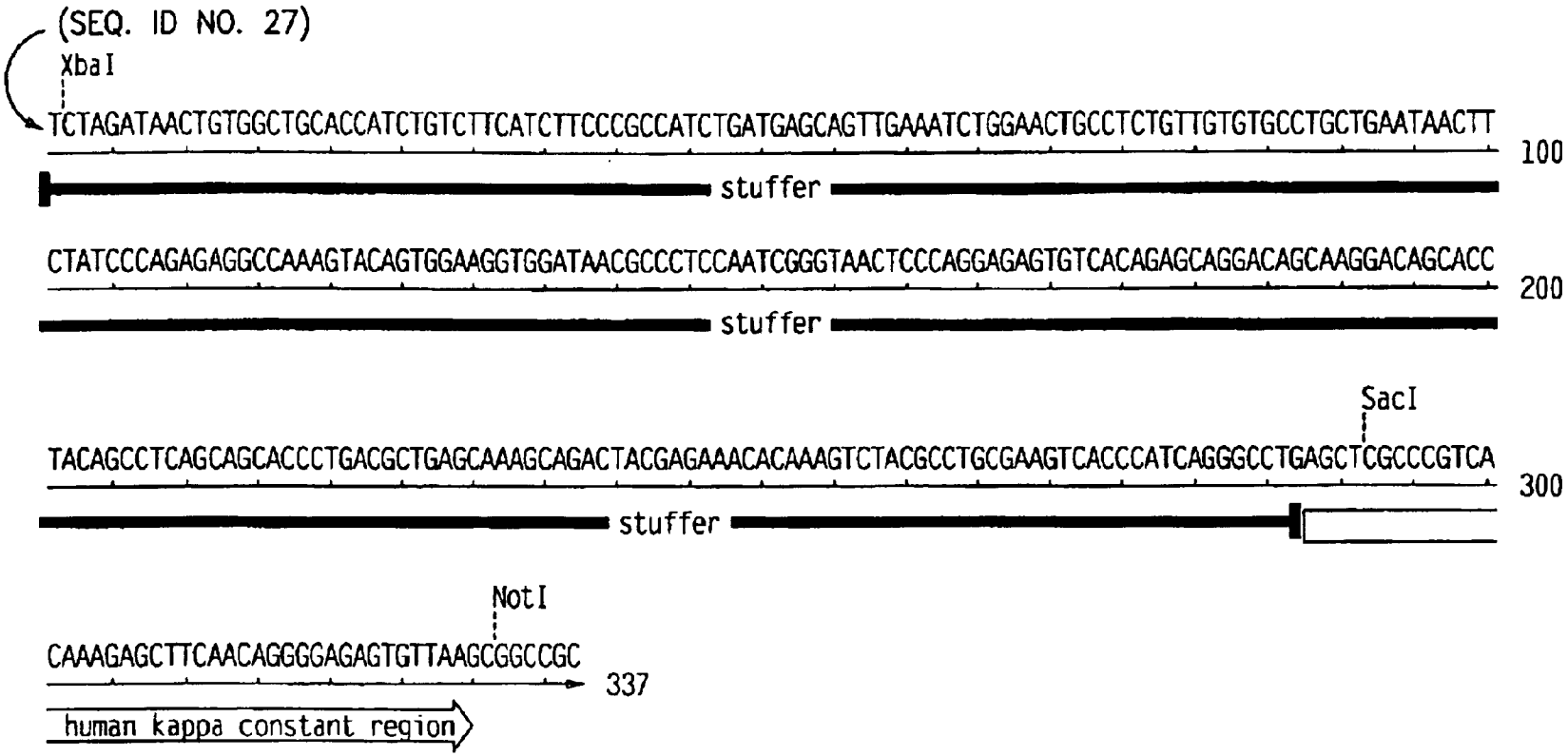
Figure 12E:
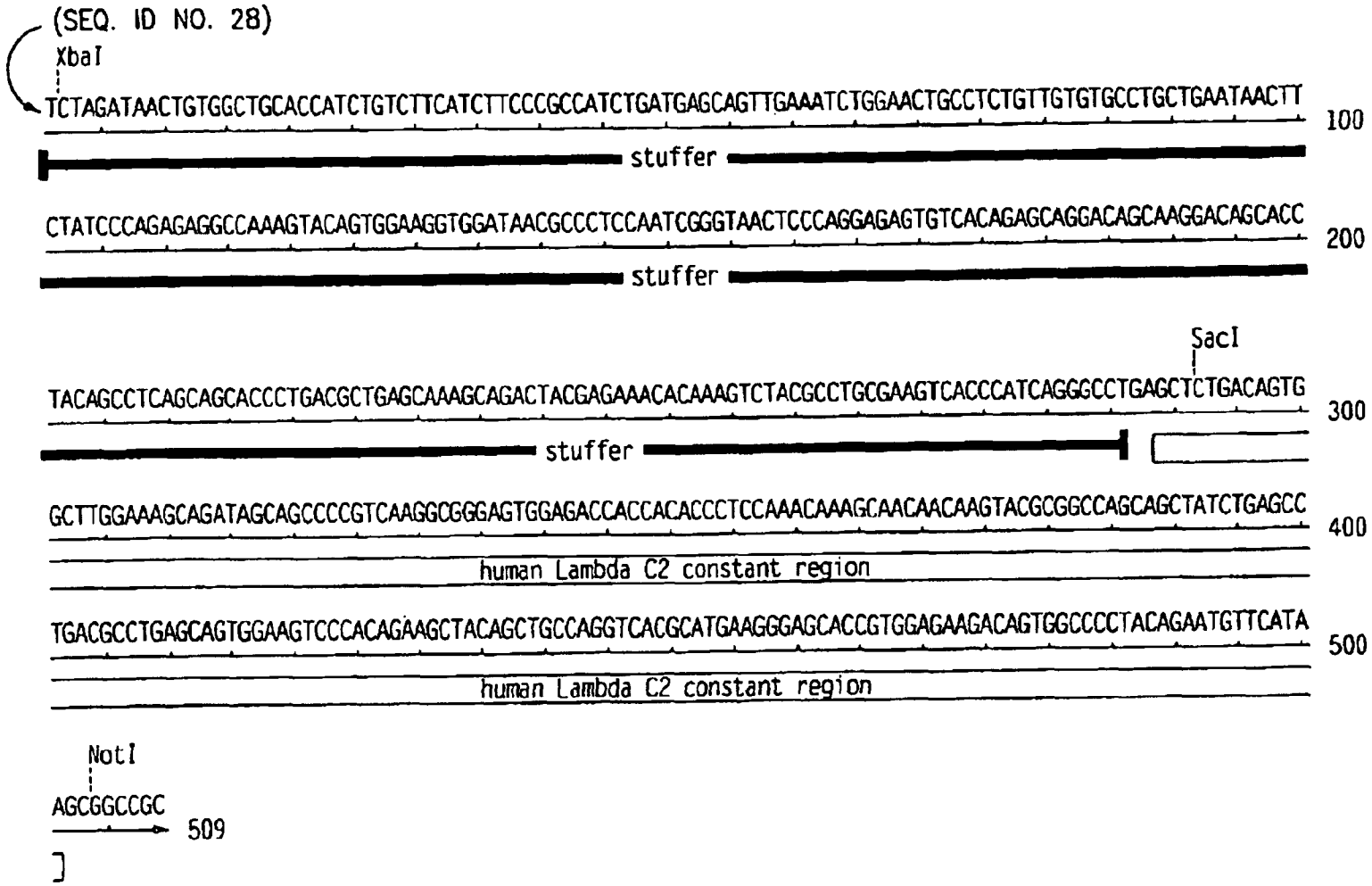
Figure 12F:
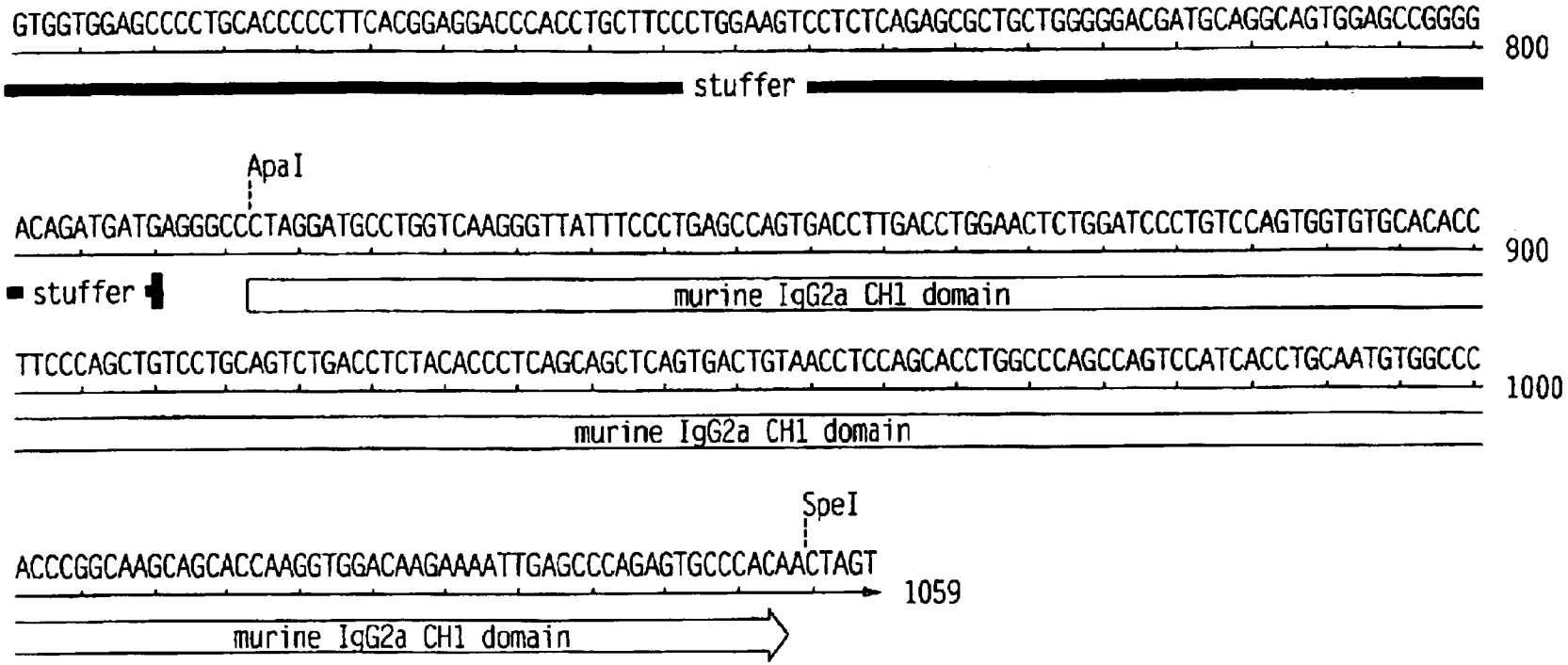
Figure 12C:
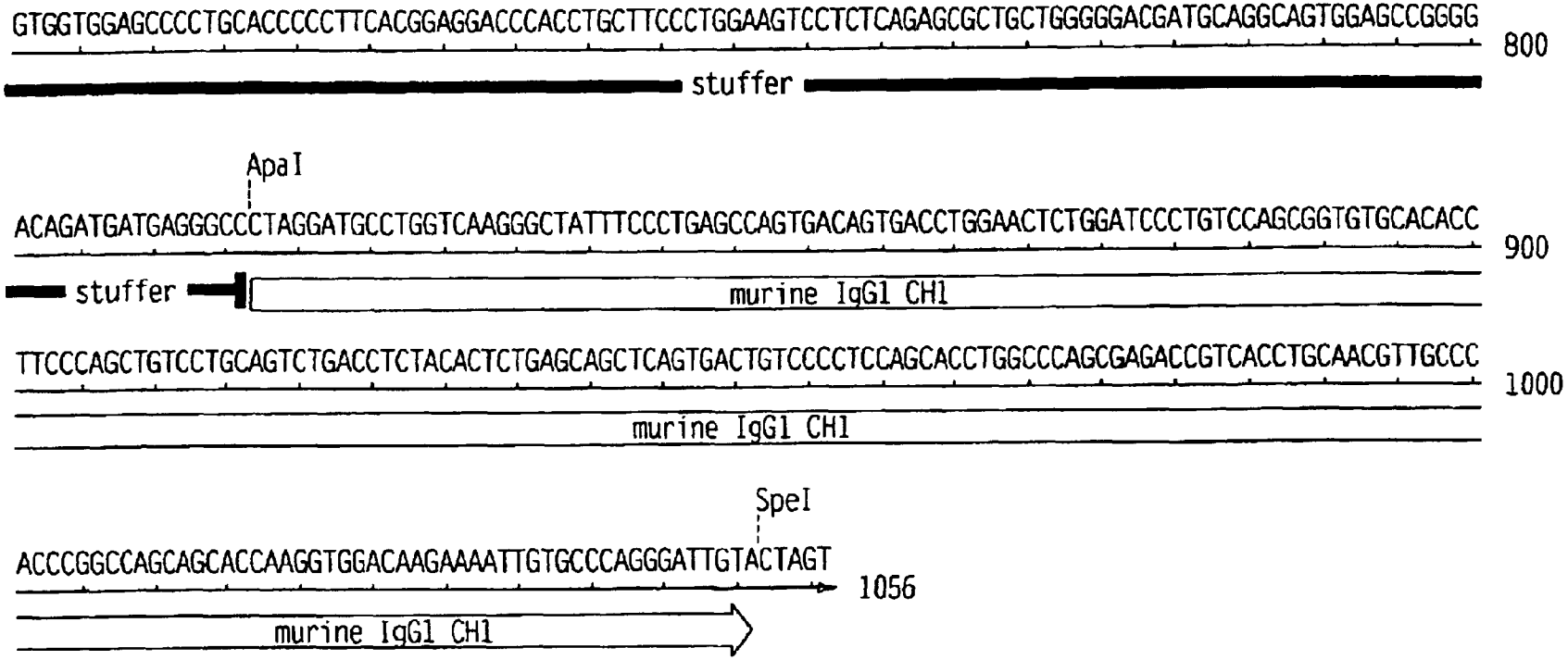

The upstream transcriptional control cassette and the downstream transcriptional control cassette were combined with intermediate plasmid p131-44.2 digested with EcoRI and XhoI in a 3-way ligation reaction to produce pAX131 (See FIG. 9). FIG. 10 is a map of the resulting pAX131 vector. The pAX131 was analyzed to determine its nucleic acid sequence (SEQ. ID. NO. 18) which is shown in FIGS. 11A–D.

EXAMPLE 2

Insertion of an alternate upstream transcriptional control cassette

PAX131 vector was digested with Not I restriction enzyme. The resulting DNA overhangs were then filled in with Klenow fragment Polymerase to blunt end the DNA followed by ligation. This was performed to remove the existing Not I site. The Not I deleted PAX131 vector was digested with EcoR I/Xba I, and ligated with a duplexed oligo containing EcoR I and Spe I overhangs (Xba I, and Spe I have compatible ends).

Eco/Spe oligo:

5' AAT TCA AGG AGT TAA TTA TGA AAA AAA CCG CGA TTG CGA TTG CGG TGG CGC TGG CGG GCT TTG CGA CCG TGG CCC AGG CGG CCT CTA GAA TCT GCG GCC GCA 3' (SEQ. ID NO. 22)

Spe/Eco oligo:

5' CTA GTG CGG CCG CAG ATT CTA GAG GCC GCC TGG GCC ACG GTC GCA AAG CCC GCC AGC GCC ACC GCA ATC GCA ATC GCG GTT TTT TTC ATA ATT AAC TCC TTG 3' (SEQ. ID NO. 23)

Figure 13B:
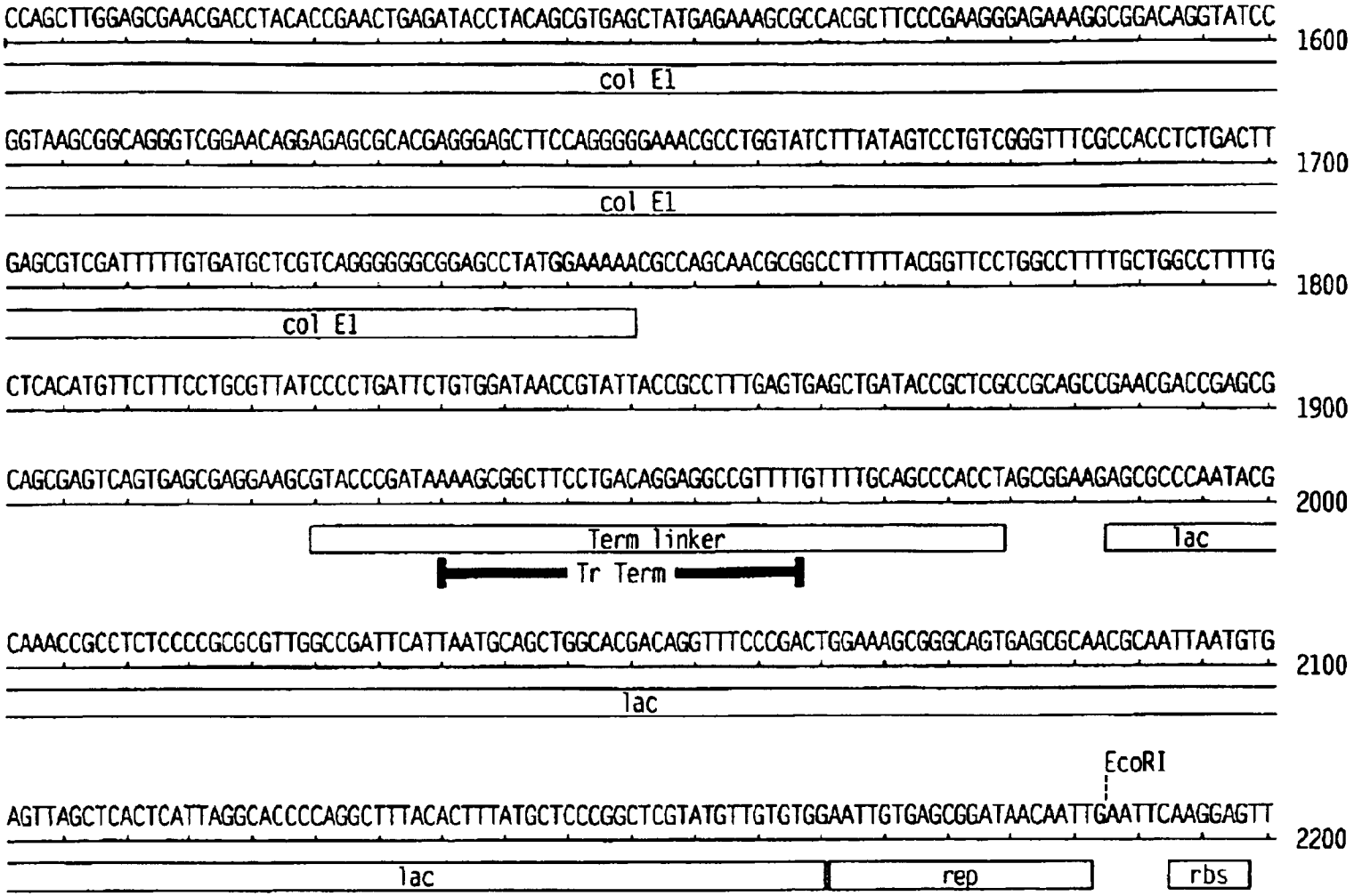
Figure 13B:
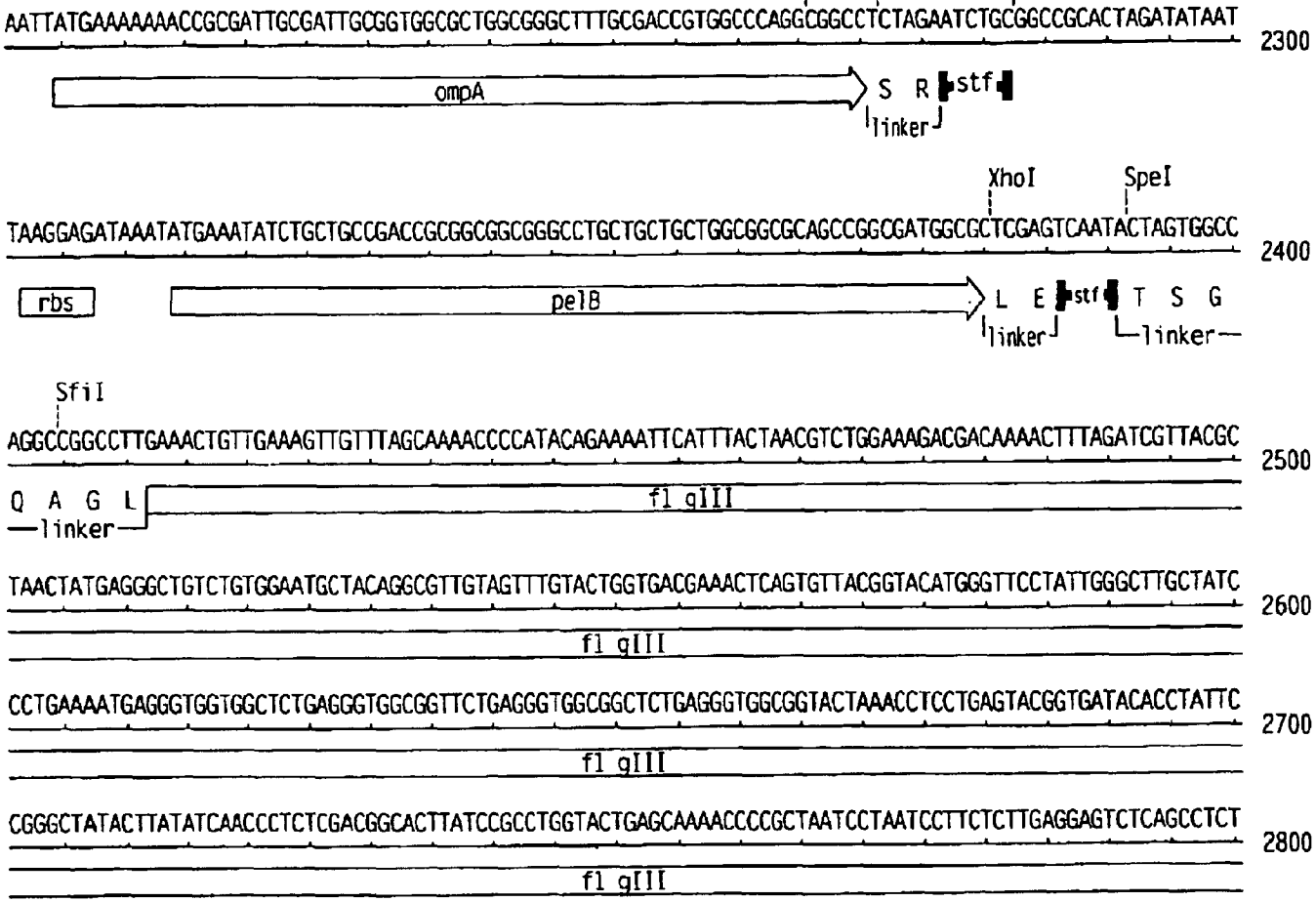
Figure 13C:
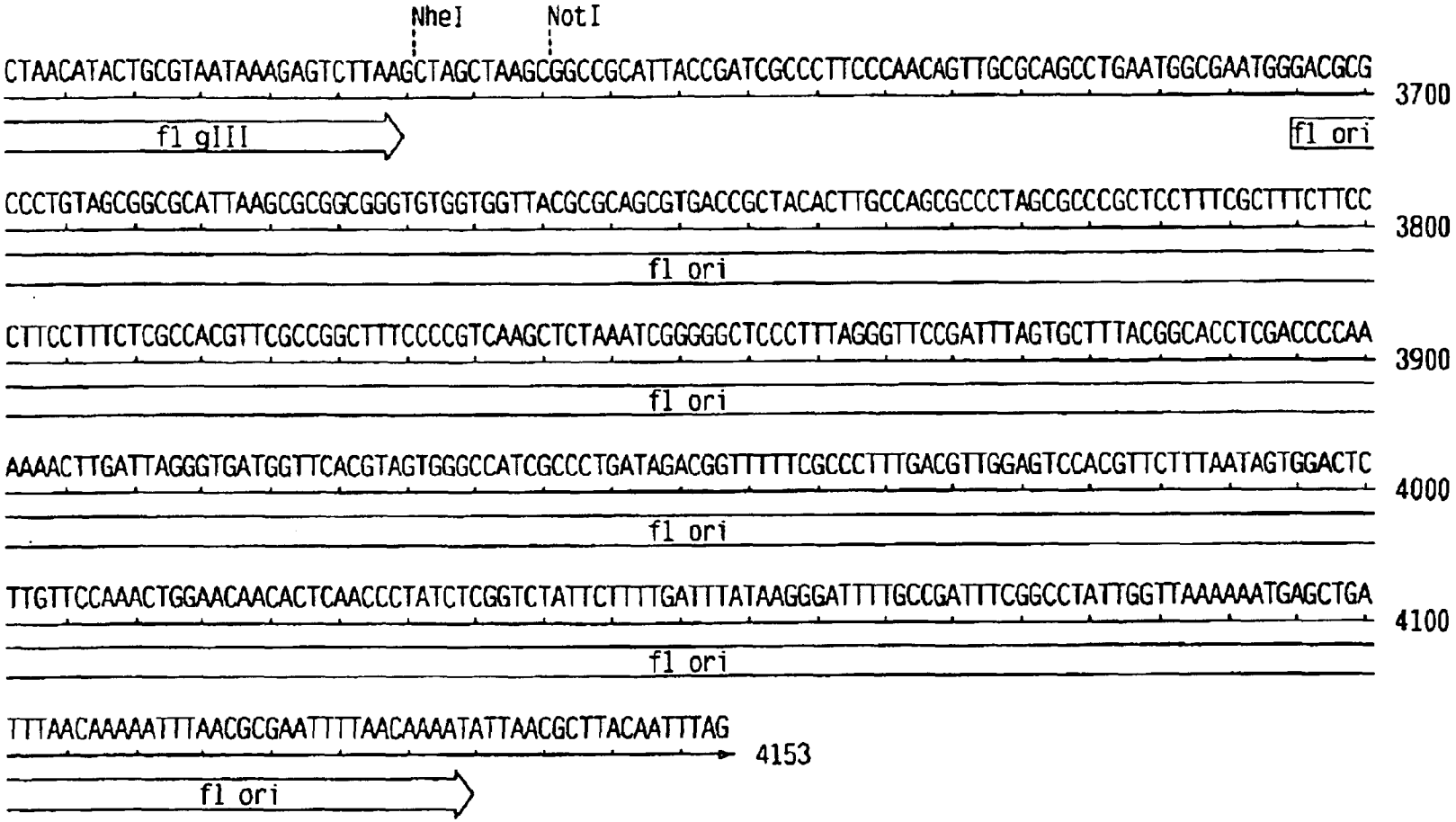

The resulting vector (pAX131 Xba/Not) had Xba I, and Not I sites for cloning of a gene, such as light chains, rather than Sac I and Xba I. FIGS. 13A–C show the nucleic acid sequence for vector (pAX131 Xba/Not.

It is contemplated that the present novel vectors can be used in connection with the production and screening of libraries made in accordance with conventional phage display technologies. Both natural and synthetic antibody repertoires have been generated as phage displayed libraries. Natural antibodies can be cloned from B-cell mRNA isolated from peripheral blood lymphocytes, bone marrow, spleen, or other lymphatic tissue of a human or non-human donor. Donors with an immune response to the antigen(s) of interest can be used to create immune antibody libraries. Alternatively, non-immune libraries may be generated from donors by isolating naive antibody B cell genes. PCR using antibody specific primers on the 18$^{st}$ strand cDNA allows the isolation of light chain and heavy chain antibody fragments which can then be cloned into the display vector.

Synthetic antibodies or antibody libraries can be made up in part or entirely with regions of synthetically derived sequence. Library diversity can be engineered within variable regions, particularly within CDRs, through the use of degenerate oligonucleotides. For example, a single Fab gene may be modified at the heavy chain CDR3 position to contain random nucleotide sequences. The random sequence can be introduced into the heavy chain gene using an oligonucleotide which contains the degenerate coding region in an overlap PCR approach. Alternatively, degenerate oligo cassettes can be cloned into restriction sites that flank the CDR(s) to create diversity. The resulting library generated by this or other approaches can then be cloned into a display vector in accordance with this disclosure.

Upon introduction of the display library into bacteria, phage particles will be generated that have antibody displayed on the surface. The resulting collection of phage-displayed antibodies can be selected for those with the ability to bind to the antigen of interest using techniques known to those skilled in the art. Antibodies identified by this system can be used therapeutically, as diagnostic reagents, or as research tools.

It is contemplated that single and double stranded versions of the vectors described herein are within the scope of the present invention. It is well within the purview of those skilled in the art to prepare either single or double stranded vectors having the features described herein.

It will be understood that various modifications may be made to the embodiments described herein. For example, as those skilled in the art will appreciate, a first gene encoding a fusion protein having an antibody light chain to be fused to and displayed by pVIII and a second gene encoding a heavy chain Fd can be inserted into the vector at the newly created restriction site to provide effective antibody display. Therefore, the above description should not be construed as limiting, but merely as exemplifications of preferred embodiments. Those skilled in the art will envision other modifications within the scope and spirit of the claims appended hereto.

SEQUENCE LISTING

```
<160> NUMBER OF SEQ ID NOS: 31

<210> SEQ ID NO 1
<211> LENGTH: 23
<212> TYPE: DNA
<213> ORGANISM: artificial sequence
<220> FEATURE:
<223> OTHER INFORMATION: primer

<400> SEQUENCE: 1
```

-continued aaccgtatta ccgcctttga gtg 23

<210> SEQ ID NO 2
<211> LENGTH: 34
<212> TYPE: DNA
<213> ORGANISM: artificial sequence
<220> FEATURE:
<223> OTHER INFORMATION: primer

<400> SEQUENCE: 2 cctgaattca attgttatcc gctcacaatt ccac 34

<210> SEQ ID NO 3
<211> LENGTH: 21
<212> TYPE: DNA
<213> ORGANISM: artificial sequence
<220> FEATURE:
<223> OTHER INFORMATION: oligonucleotide

<400> SEQUENCE: 3 cggtaatgcg gccgctacat g 21

<210> SEQ ID NO 4
<211> LENGTH: 27
<212> TYPE: DNA
<213> ORGANISM: artificial sequence
<220> FEATURE:
<223> OTHER INFORMATION: oligonucleotide

<400> SEQUENCE: 4 aattcatgta gcggccgcat taccgat 27

<210> SEQ ID NO 5
<211> LENGTH: 58
<212> TYPE: DNA
<213> ORGANISM: artificial sequence
<220> FEATURE:
<223> OTHER INFORMATION: oligonucleotide

<400> SEQUENCE: 5 agcgtacccg ataaaagcgg cttcctgaca ggaggccgtt ttgttttgca gcccacct 58

<210> SEQ ID NO 6
<211> LENGTH: 58
<212> TYPE: DNA
<213> ORGANISM: artificial sequence
<220> FEATURE:
<223> OTHER INFORMATION: oligonucleotide

<400> SEQUENCE: 6 gctaggtggg ctgcaaaaca aaacggcctc ctgtcaggaa gccgctttta tcgggtac 58

<210> SEQ ID NO 7
<211> LENGTH: 50
<212> TYPE: DNA
<213> ORGANISM: artificial sequence
<220> FEATURE:
<223> OTHER INFORMATION: oligonucleotide

<400> SEQUENCE: 7 aattcacatc tagatatctc gagtcaatac tagtggccag gccggccagc 50

<210> SEQ ID NO 8
<211> LENGTH: 50
<212> TYPE: DNA

-continued

<213> ORGANISM: artificial sequence
<220> FEATURE:
<223> OTHER INFORMATION: oligonucleotide

<400> SEQUENCE: 8 ggccgctggc cggcctggcc actagtattg actcgagata tctagatgtg 50

<210> SEQ ID NO 9
<211> LENGTH: 44
<212> TYPE: DNA
<213> ORGANISM: artificial sequence
<220> FEATURE:
<223> OTHER INFORMATION: primer

<400> SEQUENCE: 9 agtggccagg ccggccttga aactgttgaa agttgtttag caaa 44

<210> SEQ ID NO 10
<211> LENGTH: 51
<212> TYPE: DNA
<213> ORGANISM: artificial sequence
<220> FEATURE:
<223> OTHER INFORMATION: primer

<400> SEQUENCE: 10 tctgcggccg cttagctagc ttaagactct ttattacgca gtatgttagc a 51

<210> SEQ ID NO 11
<211> LENGTH: 94
<212> TYPE: DNA
<213> ORGANISM: artificial sequence
<220> FEATURE:
<223> OTHER INFORMATION: oligonucleotide

<400> SEQUENCE: 11 aattcaagga gttaattatg aaaaaaaccg cgattgcgat tgcggtggcg ctggcgggct 60 ttgcgaccgt ggcccaggcg gccgagctca tctt 94

<210> SEQ ID NO 12
<211> LENGTH: 94
<212> TYPE: DNA
<213> ORGANISM: artificial sequence
<220> FEATURE:
<223> OTHER INFORMATION: oligonucleotide

<400> SEQUENCE: 12 ctagaagatg agctcggccg cctgggccac ggtcgcaaag cccgccagcg ccaccgcaat 60 cgcaatcgcg gtttttttca taattaactc cttg 94

<210> SEQ ID NO 13
<211> LENGTH: 6
<212> TYPE: DNA
<213> ORGANISM: artificial sequence
<220> FEATURE:
<223> OTHER INFORMATION: RBS

<400> SEQUENCE: 13 aaggag 6

<210> SEQ ID NO 14
<211> LENGTH: 66
<212> TYPE: DNA
<213> ORGANISM: artificial sequence
<220> FEATURE:
<223> OTHER INFORMATION: ompA leader -continued

<400> SEQUENCE: 14 atgaaaaaaa ccgcgattgc gattgcggtg gcgctggcgg gctttgcgac cgtggcccag 60 gcggcc 66

<210> SEQ ID NO 15
<211> LENGTH: 91
<212> TYPE: DNA
<213> ORGANISM: artificial sequence
<220> FEATURE:
<223> OTHER INFORMATION: oligonucleotide

<400> SEQUENCE: 15 ctagatataa ttaaggagat aaatatgaaa tatctgctgc cgaccgcggc ggcgggcctg 60 ctgctgctgg cggcgcagcc ggcgatggcg c 91

<210> SEQ ID NO 16
<211> LENGTH: 91
<212> TYPE: DNA
<213> ORGANISM: artificial sequence
<220> FEATURE:
<223> OTHER INFORMATION: oligonucleotide

<400> SEQUENCE: 16 tcgagcgcca tcgccggctg cgccgccagc agcagcaggc ccgccgccgc ggtcggcagc 60 agatatttca tatttatctc cttaattata t 91

<210> SEQ ID NO 17
<211> LENGTH: 67
<212> TYPE: DNA
<213> ORGANISM: artificial sequence
<220> FEATURE:
<223> OTHER INFORMATION: pelB leader

<400> SEQUENCE: 17 tatgaaatat ctgctgccga ccgcggcggc gggcctgctg ctgctggcgg cgcagccggc 60 gatggcg 67

<210> SEQ ID NO 18
<211> LENGTH: 4154
<212> TYPE: DNA
<213> ORGANISM: artificial sequence
<220> FEATURE:
<223> OTHER INFORMATION: plasmid vector

<400> SEQUENCE: 18 gtggcacttt tcggggaaat gtgcgcggaa cccctatttg tttatttttc taaatacatt 60 caaatatgta tccgctcatg agacaataac cctgataaat gcttcaataa tattgaaaaa 120 ggaagagtat gagtattcaa catttccgtg tcgcccttat tccctttttt gcggcatttt 180 gccttcctgt ttttgctcac ccagaaacgc tggtgaaagt aaaagatgct gaagatcagt 240 tgggtgcacg agtgggttac atcgaactgg atctcaacag cggtaagatc cttgagagtt 300 ttcgccccga agaacgtttt ccaatgatga gcacttttaa agttctgcta tgtggcgcgg 360 tattatcccg tattgacgcc gggcaagagc aactcggtcg ccgcatacac tattctcaga 420 atgacttggt tgagtactca ccagtcacag aaaagcatct tacggatggc atgacagtaa 480 gagaattatg cagtgctgcc ataaccatga gtgataacac tgcggccaac ttacttctga 540 caacgatcgg aggaccgaag gagctaaccg ctttttttgca caacatgggg gatcatgtaa 600

-continued

```
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac gggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcgtaccc gataaaagcg gcttcctgac aggaggccgt tttgttttgc agcccaccta   1980
gcggaagagc gcccaatacg caaaccgcct ctccccgcgc gttggccgat tcattaatgc   2040
agctggcacg acaggtttcc cgactggaaa gcgggcagtg agcgcaacgc aattaatgtg   2100
agttagctca ctcattaggc accccaggct ttacacttta tgctcccggc tcgtatgttg   2160
tgtggaattg tgagcggata acaattgaat tcaaggagtt aattatgaaa aaaaccgcga   2220
ttgcgattgc ggtggcgctg gcgggctttg cgaccgtggc ccaggcggcc gagctcatct   2280
tctagatata attaaggaga taaatatgaa atatctgctg ccgaccgcgg cggcgggcct   2340
gctgctgctg gcggcgcagc cggcgatggc gctcgagtca atactagtgg ccaggccggc   2400
cttgaaactg ttgaaagttg tttagcaaaa ccccatacag aaaattcatt tactaacgtc   2460
tggaaagacg acaaaacttt agatcgttac gctaactatg agggctgtct gtggaatgct   2520
acaggcgttg tagtttgtac tggtgacgaa actcagtgtt acggtacatg ggttcctatt   2580
gggcttgcta tccctgaaaa tgagggtggt ggctctgagg gtggcggttc tgagggtggc   2640
ggctctgagg gtggcggtac taaacctcct gagtacggtg atacacctat tccgggctat   2700
acttatatca accctctcga cggcacttat ccgcctggta ctgagcaaaa ccccgctaat   2760
cctaatcctt ctcttgagga gtctcagcct cttaatactt tcatgtttca gaataatagg   2820
ttccgaaata ggcagggggc attaactgtt tatacgggca ctgttactca aggcactgac   2880
cccgttaaaa cttattacca gtacactcct gtatcatcaa aagccatgta tgacgcttac   2940
tggaacggta aattcagaga ctgcgctttc cattctggct ttaatgagga tccattcgtt   3000
```

-continued

```
tgtgaatatc aaggccaatc gtctgacctg cctcaacctc ctgttaatgc tggcggcggc   3060

tctggtggtg gttctggtgg cggctctgag ggtggtggct ctgagggtgg cggttctgag   3120

ggtggcggct ctgagggtgg cggttccggt ggtggctctg gttccggtga ttttgattat   3180

gaaaagatgg caaacgctaa taagggggct atgaccgaaa atgccgatga aaacgatgaa   3240

aacgcgctac agtctgacgc taaaggcaaa cttgattctg tcgctactga ttacggtgct   3300

gctatcgacg gtttcattgg tgacgtttcc ggccttgcta atggtaatgg tgctactggt   3360

gattttgctg gctctaattc ccaaatggct caagtcggtg acggtgataa ttcaccttta   3420

atgaataatt tccgtcaata tttaccttcc ctccctcaat cggttgaatg tcgccctttt   3480

gtctttggcg ctggtaaacc atatgaattt tctattgatt gtgacaaaat aaacttattc   3540

cgtggtgtct ttgcgtttct tttatatgtt gccaccttta tgtatgtatt ttcgacgttt   3600

gctaacatac tgcgtaataa agagtcttaa gctagctaag cggccgcatt accgatcgcc   3660

cttcccaaca gttgcgcagc ctgaatggcg aatgggacgc gccctgtagc ggcgcattaa   3720

gcgcggcggg tgtggtggtt acgcgcagcg tgaccgctac acttgccagc gccctagcgc   3780

ccgctccttt cgctttcttc ccttcctttc tcgccacgtt cgccggcttt ccccgtcaag   3840

ctctaaatcg ggggctccct ttagggttcc gatttagtgc tttacggcac ctcgacccca   3900

aaaaacttga ttagggtgat ggttcacgta gtgggccatc gccctgatag acggtttttc   3960

gccctttgac gttggagtcc acgttcttta atagtggact cttgttccaa actggaacaa   4020

cactcaaccc tatctcggtc tattcttttg atttataagg gattttgccg atttcggcct   4080

attggttaaa aaatgagctg atttaacaaa aatttaacgc gaattttaac aaaatattaa   4140

cgcttacaat ttag                                                     4154
```

```
<210> SEQ ID NO 19
<211> LENGTH: 2654
<212> TYPE: DNA
<213> ORGANISM: artificial sequence
<220> FEATURE:
<223> OTHER INFORMATION: plasmid vector

<400> SEQUENCE: 19

ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtaatgcg gccgctacat gaattcaatt gttatccgct    540

cacaattcca cacaacatac gagccggaag cataaagtgt aaagcctggg gtgcctaatg    600

agtgagctaa ctcacattaa ttgcgttgcg ctcactgccc gctttccagt cgggaaacct    660

gtcgtgccag ctgcattaat gaatcggcca acgcgcgggg agaggcggtt tgcgtattgg    720

gcgctcttcc gcttcctcgc tcactgactc gctgcgctcg gtcgttcggc tgcggcgagc    780

ggtatcagct cactcaaagg cggtaatacg gttatccaca gaatcagggg ataacgcagg    840
```

-continued

```
aaagaacatg tgagcaaaag gccagcaaaa ggccaggaac cgtaaaaagg ccgcgttgct    900

ggcgtttttc cataggctcc gcccccctga cgagcatcac aaaaatcgac gctcaagtca    960

gaggtggcga aacccgacag gactataaag ataccaggcg tttccccctg gaagctccct   1020

cgtgcgctct cctgttccga ccctgccgct taccggatac ctgtccgcct ttctcccttc   1080

gggaagcgtg gcgctttctc atagctcacg ctgtaggtat ctcagttcgg tgtaggtcgt   1140

tcgctccaag ctgggctgtg tgcacgaacc ccccgttcag cccgaccgct gcgccttatc   1200

cggtaactat cgtcttgagt ccaacccggt aagacacgac ttatcgccac tggcagcagc   1260

cactggtaac aggattagca gagcgaggta tgtaggcggt gctacagagt tcttgaagtg   1320

gtggcctaac tacggctaca ctagaaggac agtatttggt atctgcgctc tgctgaagcc   1380

agttaccttc ggaaaaagag ttggtagctc ttgatccggc aaacaaacca ccgctggtag   1440

cggtggtttt tttgtttgca agcagcagat tacgcgcaga aaaaaaggat ctcaagaaga   1500

tcctttgatc ttttctacgg ggtctgacgc tcagtggaac gaaaactcac gttaagggat   1560

tttggtcatg agattatcaa aaaggatctt cacctagatc cttttaaatt aaaaatgaag   1620

ttttaaatca atctaaagta tatatgagta aacttggtct gacagttacc aatgcttaat   1680

cagtgaggca cctatctcag cgatctgtct atttcgttca tccatagttg cctgactccc   1740

cgtcgtgtag ataactacga tacgggaggg cttaccatct ggccccagtg ctgcaatgat   1800

accgcgagac ccacgctcac cggctccaga tttatcagca ataaaccagc cagccggaag   1860

ggccgagcgc agaagtggtc ctgcaacttt atccgcctcc atccagtcta ttaattgttg   1920

ccgggaagct agagtaagta gttcgccagt taatagtttg cgcaacgttg ttgccattgc   1980

tacaggcatc gtggtgtcac gctcgtcgtt tggtatggct tcattcagct ccggttccca   2040

acgatcaagg cgagttacat gatcccccat gttgtgcaaa aaagcggtta gctccttcgg   2100

tcctccgatc gttgtcagaa gtaagttggc cgcagtgtta tcactcatgg ttatggcagc   2160

actgcataat tctcttactg tcatgccatc cgtaagatgc ttttctgtga ctggtgagta   2220

ctcaaccaag tcattctgag aatagtgtat gcggcgaccg agttgctctt gcccggcgtc   2280

aatacgggat aataccgcgc cacatagcag aactttaaaa gtgctcatca ttggaaaacg   2340

ttcttcgggg cgaaaactct caaggatctt accgctgttg agatccagtt cgatgtaacc   2400

cactcgtgca cccaactgat cttcagcatc ttttactttc accagcgttt ctgggtgagc   2460

aaaaacagga aggcaaaatg ccgcaaaaaa gggaataagg gcgacacgga aatgttgaat   2520

actcatactc ttcctttttc aatattattg aagcatttat cagggttatt gtctcatgag   2580

cggatacata tttgaatgta tttagaaaaa taaacaaata ggggttccgc gcacatttcc   2640

ccgaaaagtg ccac                                                     2654
```

<210> SEQ ID NO 20
<211> LENGTH: 2712
<212> TYPE: DNA
<213> ORGANISM: artificial sequence
<220> FEATURE:
<223> OTHER INFORMATION: plasmid vector

<400> SEQUENCE: 20

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240
```

-continued

```
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtaatgcg gccgctacat gaattcaatt gttatccgct    540
cacaattcca cacaacatac gagccgggag cataaagtgt aaagcctggg gtgcctaatg    600
agtgagctaa ctcacattaa ttgcgttgcg ctcactgccc gctttccagt cgggaaacct    660
gtcgtgccag ctgcattaat gaatcggcca acgcgcgggg agaggcggtt tgcgtattgg    720
gcgctcttcc gctaggtggg ctgcaaaaca aaacggcctc ctgtcaggaa gccgctttta    780
tcgggtacgc ttcctcgctc actgactcgc tgcgctcggt cgttcggctg cggcgagcgg    840
tatcagctca ctcaaaggcg gtaatacggt tatccacaga atcaggggat aacgcaggaa    900
agaacatgtg agcaaaaggc cagcaaaagg ccaggaaccg taaaaaggcc gcgttgctgg    960
cgtttttcca taggctccgc ccccctgacg agcatcacaa aaatcgacgc tcaagtcaga   1020
ggtggcgaaa cccgacagga ctataaagat accaggcgtt tccccctgga agctccctcg   1080
tgcgctctcc tgttccgacc ctgccgctta ccggatacct gtccgccttt ctcccttcgg   1140
gaagcgtggc gctttctcat agctcacgct gtaggtatct cagttcggtg taggtcgttc   1200
gctccaagct gggctgtgtg cacgaacccc ccgttcagcc cgaccgctgc gccttatccg   1260
gtaactatcg tcttgagtcc aacccggtaa gacacgactt atcgccactg gcagcagcca   1320
ctggtaacag gattagcaga gcgaggtatg taggcggtgc tacagagttc ttgaagtggt   1380
ggcctaacta cggctacact agaaggacag tatttggtat ctgcgctctg ctgaagccag   1440
ttaccttcgg aaaaagagtt ggtagctctt gatccggcaa acaaaccacc gctggtagcg   1500
gtggtttttt tgtttgcaag cagcagatta cgcgcagaaa aaaaggatct caagaagatc   1560
ctttgatctt ttctacgggg tctgacgctc agtggaacga aaactcacgt taagggattt   1620
tggtcatgag attatcaaaa aggatcttca cctagatcct tttaaattaa aaatgaagtt   1680
ttaaatcaat ctaaagtata tatgagtaaa cttggtctga cagttaccaa tgcttaatca   1740
gtgaggcacc tatctcagcg atctgtctat ttcgttcatc catagttgcc tgactccccg   1800
tcgtgtagat aactacgata cgggagggct taccatctgg ccccagtgct gcaatgatac   1860
cgcgagaccc acgctcaccg gctccagatt tatcagcaat aaaccagcca gccggaaggg   1920
ccgagcgcag aagtggtcct gcaactttat ccgcctccat ccagtctatt aattgttgcc   1980
gggaagctag agtaagtagt tcgccagtta atagtttgcg caacgttgtt gccattgcta   2040
caggcatcgt ggtgtcacgc tcgtcgtttg gtatggcttc attcagctcc ggttcccaac   2100
gatcaaggcg agttacatga tcccccatgt tgtgcaaaaa agcggttagc tccttcggtc   2160
ctccgatcgt tgtcagaagt aagttggccg cagtgttatc actcatggtt atggcagcac   2220
tgcataattc tcttactgtc atgccatccg taagatgctt ttctgtgact ggtgagtact   2280
caaccaagtc attctgagaa tagtgtatgc ggcgaccgag ttgctcttgc ccggcgtcaa   2340
tacgggataa taccgcgcca catagcagaa ctttaaaagt gctcatcatt ggaaaacgtt   2400
cttcggggcg aaaactctca aggatcttac cgctgttgag atccagttcg atgtaaccca   2460
ctcgtgcacc caactgatct tcagcatctt ttactttcac cagcgtttct gggtgagcaa   2520
aaacaggaag gcaaaatgcc gcaaaaaagg gaataagggc gacacggaaa tgttgaatac   2580
```

-continued

```
tcatactctt ccttttcaa tattattgaa gcatttatca gggttattgt ctcatgagcg   2640

gatacatatt tgaatgtatt tagaaaaata aacaaatagg ggttccgcgc acatttcccc   2700

gaaaagtgcc ac                                                       2712


<210> SEQ ID NO 21
<211> LENGTH: 2750
<212> TYPE: DNA
<213> ORGANISM: artificial sequence
<220> FEATURE:
<223> OTHER INFORMATION: plasmid vector

<400> SEQUENCE: 21

gtggcacttt tcggggaaat gtgcgcggaa cccctatttg tttatttttc taaatacatt     60

caaatatgta tccgctcatg agacaataac cctgataaat gcttcaataa tattgaaaaa    120

ggaagagtat gagtattcaa catttccgtg tcgcccttat tccctttttt gcggcatttt    180

gccttcctgt ttttgctcac ccagaaacgc tggtgaaagt aaaagatgct gaagatcagt    240

tgggtgcacg agtgggttac atcgaactgg atctcaacag cggtaagatc cttgagagtt    300

ttcgccccga agaacgtttt ccaatgatga gcacttttaa agttctgcta tgtggcgcgg    360

tattatcccg tattgacgcc gggcaagagc aactcggtcg ccgcatacac tattctcaga    420

atgacttggt tgagtactca ccagtcacag aaaagcatct tacggatggc atgacagtaa    480

gagaattatg cagtgctgcc ataaccatga gtgataacac tgcggccaac ttacttctga    540

caacgatcgg aggaccgaag gagctaaccg ctttttgca caacatgggg gatcatgtaa    600

ctcgccttga tcgttgggaa ccggagctga atgaagccat accaaacgac gagcgtgaca    660

ccacgatgcc tgtagcaatg gcaacaacgt tgcgcaaact attaactggc gaactactta    720

ctctagcttc ccggcaacaa ttaatagact ggatggaggc ggataaagtt gcaggaccac    780

ttctgcgctc ggcccttccg gctggctggt ttattgctga taaatctgga gccggtgagc    840

gtgggtctcg cggtatcatt gcagcactgg ggccagatgg taagccctcc cgtatcgtag    900

ttatctacac gacggggagt caggcaacta tggatgaacg aaatagacag atcgctgaga    960

taggtgcctc actgattaag cattggtaac tgtcagacca agtttactca tatatacttt   1020

agattgattt aaaacttcat ttttaattta aaaggatcta ggtgaagatc ctttttgata   1080

atctcatgac caaaatccct taacgtgagt tttcgttcca ctgagcgtca gaccccgtag   1140

aaaagatcaa aggatcttct tgagatcctt tttttctgcg cgtaatctgc tgcttgcaaa   1200

caaaaaaacc accgctacca gcggtggttt gtttgccgga tcaagagcta ccaactcttt   1260

ttccgaaggt aactggcttc agcagagcgc agataccaaa tactgtcctt ctagtgtagc   1320

cgtagttagg ccaccacttc aagaactctg tagcaccgcc tacatacctc gctctgctaa   1380

tcctgttacc agtggctgct gccagtggcg ataagtcgtg tcttaccggg ttggactcaa   1440

gacgatagtt accggataag gcgcagcggt cgggctgaac gggggggttcg tgcacacagc   1500

ccagcttgga gcgaacgacc tacaccgaac tgagatacct acagcgtgag ctatgagaaa   1560

gcgccacgct tcccgaaggg agaaaggcgg acaggtatcc ggtaagcggc agggtcggaa   1620

caggagagcg cacgagggag cttccagggg gaaacgcctg gtatctttat agtcctgtcg   1680

ggtttcgcca cctctgactt gagcgtcgat ttttgtgatg ctcgtcaggg gggcggagcc   1740

tatggaaaaa cgccagcaac gcggcctttt tacggttcct ggccttttgc tggccttttg   1800

ctcacatgtt ctttcctgcg ttatcccctg attctgtgga taaccgtatt accgcctttg   1860

agtgagctga taccgctcgc cgcagccgaa cgaccgagcg cagcgagtca gtgagcgagg   1920
```

-continued

```
aagcgtaccc gataaaagcg gcttcctgac aggaggccgt tttgttttgc agcccaccta   1980

gcggaagagc gcccaatacg caaaccgcct ctccccgcgc gttggccgat tcattaatgc   2040

agctggcacg acaggtttcc cgactggaaa gcgggcagtg agcgcaacgc aattaatgtg   2100

agttagctca ctcattaggc accccaggct ttacacttta tgctcccggc tcgtatgttg   2160

tgtggaattg tgagcggata acaattgaat tcacatctag atatctcgag tcaatactag   2220

tggccaggcc ggccagcggc cgcattaccg atcgcccttc ccaacagttg cgcagcctga   2280

atggcgaatg ggacgcgccc tgtagcggcg cattaagcgc ggcgggtgtg gtggttacgc   2340

gcagcgtgac cgctacactt gccagcgccc tagcgcccgc tcctttcgct ttcttccctt   2400

cctttctcgc cacgttcgcc ggctttcccc gtcaagctct aaatcggggg ctccctttag   2460

ggttccgatt tagtgcttta cggcacctcg accccaaaaa acttgattag ggtgatggtt   2520

cacgtagtgg gccatcgccc tgatagacgg tttttcgccc tttgacgttg gagtccacgt   2580

tctttaatag tggactcttg ttccaaactg gaacaacact caaccctatc tcggtctatt   2640

cttttgattt ataagggatt ttgccgattt cggcctattg gttaaaaaat gagctgattt   2700

aacaaaaatt taacgcgaat tttaacaaaa tattaacgct tacaatttag              2750
```

<210> SEQ ID NO 22
<211> LENGTH: 102
<212> TYPE: DNA
<213> ORGANISM: artificial sequence
<220> FEATURE:
<223> OTHER INFORMATION: oligonucleotide

<400> SEQUENCE: 22

```
aattcaagga gttaattatg aaaaaaaccg cgattgcgat tgcggtggcg ctggcgggct     60

ttgcgaccgt ggcccaggcg gcctctagaa tctgcggccg ca                       102
```

<210> SEQ ID NO 23
<211> LENGTH: 102
<212> TYPE: DNA
<213> ORGANISM: artificial sequence
<220> FEATURE:
<223> OTHER INFORMATION: oligonucleotide

<400> SEQUENCE: 23

```
ctagtgcggc cgcagattct agaggccgcc tgggccacgg tcgcaaagcc cgccagcgcc     60

accgcaatcg caatcgcggt ttttttcata attaactcct tg                       102
```

<210> SEQ ID NO 24
<211> LENGTH: 565
<212> TYPE: DNA
<213> ORGANISM: artificial sequence
<220> FEATURE:
<223> OTHER INFORMATION: stuffer sequence

<400> SEQUENCE: 24

```
tctagataac tgtggctgca ccatctgtct tcatcttccc gccatctgat gagcagttga     60

aatctggaac tgcctctgtt gtgtgcctgc tgaataactt ctatcccaga gaggccaaag    120

tacagtggaa ggtggataac gccctccaat cgggtaactc ccaggagagt gtcacagagc    180

aggacagcaa ggacagcacc tacagcctca gcagcaccct gacgctgagc aaagcagact    240

acgagaaaca caaagtctac gcctgcgaag tcacccatca gggcctgagc tccggaggtg    300

cctcagtcgt gtgcttcttg aacaacttct accccaaaga catcaatgtc aagtggaaga    360
```

-continued

```
ttgatggcag tgaacgacaa aatggcgtcc tgaacagttg gactgatcag gacagcaaag    420

acagcaccta cagcatgagc agcaccctca cgttgaccaa ggacgagtat gaacgacata    480

acagctatac ctgtgaggcc actcacaaga catcaacttc acccattgtc aagagcttca    540

acaggaatga gtgttaagcg gccgc                                          565
```

<210> SEQ ID NO 25
<211> LENGTH: 1131
<212> TYPE: DNA
<213> ORGANISM: artificial sequence
<220> FEATURE:
<223> OTHER INFORMATION: stuffer sequence

<400> SEQUENCE: 25

```
ctcgagctga tgagccatgg aagctgtgtc gcctgcacca ggctcccacg gctcgtggtg     60

cggtgcgctt ctggtgttcg ctgcctacag ccgacacgtc gagcttcgtg cccctagagt    120

tgcgcgtcac agcagcctcc ggcgctccgc gatatcaccg tgtcatccac atcaatgaag    180

tagtgctcct agacgccccc gtggggctgg tggcgcggtt ggctgacgag agcggccacg    240

tagtgttgcg ctggctcccg ccgcctgaga cacccatgac gtctcacatc cgctacgagg    300

tggacgtctc ggccggcaac ggcgcaggga gcgtacagag ggtggagatc ctggagggcc    360

gcaccgagtg tgtgctgagc aacctgcggg gccggacgcg ctacaccttc gccgtccgcg    420

cgcgtatggc tgagccgagc ttcggcggct tctggagcgc ctggtcggag cctgtgtcgc    480

tgctgacgcc tagcgacctg gacccccctca tcctgacgct ctccctcatc ctcgtggtca    540

tcctggtgct gctgaccgtg ctcgcgctgc tctcccaccg ccgggctctg aagcagaaga    600

tctggcctgg catcccgagc ccagagagcg agtttgaagg cctcttcacc acccacaagg    660

gtaacttcca gctgtggctg taccagaatg atggctgcct gtggtggagc ccctgcaccc    720

ccttcacgga ggacccacct gcttccctgg aagtcctctc agagcgctgc tgggggacga    780

tgcaggcagt ggagccgggg acagatgatg agggcccttt tccccctcgt ctcctgtgag    840

aattccccgt cggatacgag cagcgtggcc gttggctgcc tcgcacagga cttccttccc    900

gactccatca ctttctcctg gaaatacaag aacaactctg acatcagcag cacccggggc    960

ttcccatcag tcctgagagg gggcaagtac gcagccacct cacaggtgct gctgccttcc   1020

aaggacgtca tgcagggcac agacgaacac gtggtgtgca aagtccagca ccccaacggc   1080

aacaaagaaa agaacgtgcc tcttccagtg attgctgagc tgcctactag t            1131
```

<210> SEQ ID NO 26
<211> LENGTH: 1121
<212> TYPE: DNA
<213> ORGANISM: artificial sequence
<220> FEATURE:
<223> OTHER INFORMATION: stuffer sequence

<400> SEQUENCE: 26

```
ctcgagctga tgagccatgg aagctgtgtc gcctgcacca ggctcccacg gctcgtggtg     60

cggtgcgctt ctggtgttcg ctgcctacag ccgacacgtc gagcttcgtg cccctagagt    120

tgcgcgtcac agcagcctcc ggcgctccgc gatatcaccg tgtcatccac atcaatgaag    180

tagtgctcct agacgccccc gtggggctgg tggcgcggtt ggctgacgag agcggccacg    240

tagtgttgcg ctggctcccg ccgcctgaga cacccatgac gtctcacatc cgctacgagg    300

tggacgtctc ggccggcaac ggcgcaggga gcgtacagag ggtggagatc ctggagggcc    360

gcaccgagtg tgtgctgagc aacctgcggg gccggacgcg ctacaccttc gccgtccgcg    420
```

-continued

```
cgcgtatggc tgagccgagc ttcggcggct tctggagcgc ctggtcggag cctgtgtcgc    480

tgctgacgcc tagcgacctg gaccccctca tcctgacgct ctccctcatc ctcgtggtca    540

tcctggtgct gctgaccgtg ctcgcgctgc tctcccaccg ccgggctctg aagcagaaga    600

tctggcctgg catcccgagc ccagagagcg agtttgaagg cctcttcacc acccacaagg    660

gtaacttcca gctgtggctg taccagaatg atggctgcct gtggtggagc ccctgcaccc    720

ccttcacgga ggacccacct gcttccctgg aagtcctctc agagcgctgc tgggggacga    780

tgcaggcagt ggagccgggg acagatgatg agggcccatc ggtcttcccc ctggcaccct    840

cctccaagag cacctctggc ggcacagcgg ccctgggctg cctggtcaag gactacttcc    900

ccgaaccggt gacggtgtcg tggaactcag gcgctctgac cagcggcgtg cacaccttcc    960

cggctgtcct acagtcctca ggactctact ccctcagcag cgtggtgacc gtgccatcca   1020

gcagcttggg cacccagacc tacatctgca acgtgaatca caagcccagc aacaccaagg   1080

tggacaagaa agttgagccc aaatcttgtg acaaaactag t                       1121
```

<210> SEQ ID NO 27
<211> LENGTH: 337
<212> TYPE: DNA
<213> ORGANISM: artificial sequence
<220> FEATURE:
<223> OTHER INFORMATION: stuffer sequence

<400> SEQUENCE: 27

```
tctagataac tgtggctgca ccatctgtct tcatcttccc gccatctgat gagcagttga     60

aatctggaac tgcctctgtt gtgtgcctgc tgaataactt ctatcccaga gaggccaaag    120

tacagtggaa ggtggataac gccctccaat cgggtaactc ccaggagagt gtcacagagc    180

aggacagcaa ggacagcacc tacagcctca gcagcaccct gacgctgagc aaagcagact    240

acgagaaaca caaagtctac gcctgcgaag tcacccatca gggcctgagc tcgcccgtca    300

caaagagctt caacagggga gagtgttaag cggccgc                             337
```

<210> SEQ ID NO 28
<211> LENGTH: 509
<212> TYPE: DNA
<213> ORGANISM: artificial sequence
<220> FEATURE:
<223> OTHER INFORMATION: stuffer sequence

<400> SEQUENCE: 28

```
tctagataac tgtggctgca ccatctgtct tcatcttccc gccatctgat gagcagttga     60

aatctggaac tgcctctgtt gtgtgcctgc tgaataactt ctatcccaga gaggccaaag    120

tacagtggaa ggtggataac gccctccaat cgggtaactc ccaggagagt gtcacagagc    180

aggacagcaa ggacagcacc tacagcctca gcagcaccct gacgctgagc aaagcagact    240

acgagaaaca caaagtctac gcctgcgaag tcacccatca gggcctgagc tctgacagtg    300

gcttggaaag cagatagcag ccccgtcaag gcgggagtgg agaccaccac accctccaaa    360

caaagcaaca acaagtacgc ggccagcagc tatctgagcc tgacgcctga gcagtggaag    420

tcccacagaa gctacagctg ccaggtcacg catgaaggga gcaccgtgga gaagacagtg    480

gcccctacag aatgttcata agcggccgc                                      509
```

<210> SEQ ID NO 29
<211> LENGTH: 1059
<212> TYPE: DNA
<213> ORGANISM: artificial sequence -continued <220> FEATURE:
<223> OTHER INFORMATION: stuffer sequence

<400> SEQUENCE: 29 ctcgagctga tgagccatgg aagctgtgtc gcctgcacca ggctcccacg gctcgtggtg 60 cggtgcgctt ctggtgttcg ctgcctacag ccgacacgtc gagcttcgtg cccctagagt 120 tgcgcgtcac agcagcctcc ggcgctccgc gatatcaccg tgtcatccac atcaatgaag 180 tagtgctcct agacgccccc gtggggctgg tggcgcggtt ggctgacgag agcggccacg 240 tagtgttgcg ctggctcccg ccgcctgaga cacccatgac gtctcacatc cgctacgagg 300 tggacgtctc ggccggcaac ggcgcaggga gcgtacagag ggtggagatc ctggagggcc 360 gcaccgagtg tgtgctgagc aacctgcggg gccggacgcg ctacaccttc gccgtccgcg 420 cgcgtatggc tgagccgagc ttcggcggct tctggagcgc ctggtcggag cctgtgtcgc 480 tgctgacgcc tagcgacctg gacccccctca tcctgacgct ctccctcatc ctcgtggtca 540 tcctggtgct gctgaccgtg ctcgcgctgc tctcccaccg ccgggctctg aagcagaaga 600 tctggcctgg catcccgagc ccagagagcg agtttgaagg cctcttcacc acccacaagg 660 gtaacttcca gctgtggctg taccagaatg atggctgcct gtggtggagc ccctgcaccc 720 ccttcacgga ggacccacct gcttccctgg aagtcctctc agagcgctgc tgggggacga 780 tgcaggcagt ggagccgggg acagatgatg agggccctag gatgcctggt caagggttat 840 ttccctgagc cagtgacctt gacctggaac tctggatccc tgtccagtgg tgtgcacacc 900 ttcccagctg tcctgcagtc tgacctctac accctcagca gctcagtgac tgtaacctcc 960 agcacctggc ccagccagtc catcacctgc aatgtggccc acccggcaag cagcaccaag 1020 gtggacaaga aaattgagcc cagagtgccc acaactagt 1059

<210> SEQ ID NO 30
<211> LENGTH: 1056
<212> TYPE: DNA
<213> ORGANISM: artificial sequence
<220> FEATURE:
<223> OTHER INFORMATION: stuffer sequence

<400> SEQUENCE: 30 ctcgagctga tgagccatgg aagctgtgtc gcctgcacca ggctcccacg gctcgtggtg 60 cggtgcgctt ctggtgttcg ctgcctacag ccgacacgtc gagcttcgtg cccctagagt 120 tgcgcgtcac agcagcctcc ggcgctccgc gatatcaccg tgtcatccac atcaatgaag 180 tagtgctcct agacgccccc gtggggctgg tggcgcggtt ggctgacgag agcggccacg 240 tagtgttgcg ctggctcccg ccgcctgaga cacccatgac gtctcacatc cgctacgagg 300 tggacgtctc ggccggcaac ggcgcaggga gcgtacagag ggtggagatc ctggagggcc 360 gcaccgagtg tgtgctgagc aacctgcggg gccggacgcg ctacaccttc gccgtccgcg 420 cgcgtatggc tgagccgagc ttcggcggct tctggagcgc ctggtcggag cctgtgtcgc 480 tgctgacgcc tagcgacctg gacccccctca tcctgacgct ctccctcatc ctcgtggtca 540 tcctggtgct gctgaccgtg ctcgcgctgc tctcccaccg ccgggctctg aagcagaaga 600 tctggcctgg catcccgagc ccagagagcg agtttgaagg cctcttcacc acccacaagg 660 gtaacttcca gctgtggctg taccagaatg atggctgcct gtggtggagc ccctgcaccc 720 ccttcacgga ggacccacct gcttccctgg aagtcctctc agagcgctgc tgggggacga 780 tgcaggcagt ggagccgggg acagatgatg agggccctag gatgcctggt caagggctat 840

-continued

```
ttccctgagc cagtgacagt gacctggaac tctggatccc tgtccagcgg tgtgcacacc    900

ttcccagctg tcctgcagtc tgacctctac actctgagca gctcagtgac tgtcccctcc    960

agcacctggc ccagcgagac cgtcacctgc aacgttgccc acccggccag cagcaccaag   1020

gtggacaaga aaattgtgcc cagggattgt actagt                             1056


<210> SEQ ID NO 31
<211> LENGTH: 4153
<212> TYPE: DNA
<213> ORGANISM: artificial sequence
<220> FEATURE:
<223> OTHER INFORMATION: plasmid vector

<400> SEQUENCE: 31

gtggcacttt tcggggaaat gtgcgcggaa cccctatttg tttatttttc taaatacatt     60

caaatatgta tccgctcatg agacaataac cctgataaat gcttcaataa tattgaaaaa    120

ggaagagtat gagtattcaa catttccgtg tcgcccttat tccctttttt gcggcatttt    180

gccttcctgt ttttgctcac ccagaaacgc tggtgaaagt aaaagatgct gaagatcagt    240

tgggtgcacg agtgggttac atcgaactgg atctcaacag cggtaagatc cttgagagtt    300

ttcgccccga agaacgtttt ccaatgatga gcacttttaa agttctgcta tgtggcgcgg    360

tattatcccg tattgacgcc gggcaagagc aactcggtcg ccgcatacac tattctcaga    420

atgacttggt tgagtactca ccagtcacag aaaagcatct tacggatggc atgacagtaa    480

gagaattatg cagtgctgcc ataaccatga gtgataacac tgcggccaac ttacttctga    540

caacgatcgg aggaccgaag gagctaaccg cttttttgca caacatgggg gatcatgtaa    600

ctcgccttga tcgttgggaa ccggagctga atgaagccat accaaacgac gagcgtgaca    660

ccacgatgcc tgtagcaatg gcaacaacgt tgcgcaaact attaactggc gaactactta    720

ctctagcttc ccggcaacaa ttaatagact ggatggaggc ggataaagtt gcaggaccac    780

ttctgcgctc ggcccttccg gctggctggt ttattgctga taaatctgga gccggtgagc    840

gtgggtctcg cggtatcatt gcagcactgg ggccagatgg taagccctcc cgtatcgtag    900

ttatctacac gacggggagt caggcaacta tggatgaacg aaatagacag atcgctgaga    960

taggtgcctc actgattaag cattggtaac tgtcagacca agtttactca tatatacttt   1020

agattgattt aaaacttcat ttttaattta aaaggatcta ggtgaagatc ctttttgata   1080

atctcatgac caaaatccct taacgtgagt tttcgttcca ctgagcgtca gaccccgtag   1140

aaaagatcaa aggatcttct tgagatcctt tttttctgcg cgtaatctgc tgcttgcaaa   1200

caaaaaaacc accgctacca gcggtggttt gtttgccgga tcaagagcta ccaactcttt   1260

ttccgaaggt aactggcttc agcagagcgc agataccaaa tactgtcctt ctagtgtagc   1320

cgtagttagg ccaccacttc aagaactctg tagcaccgcc tacatacctc gctctgctaa   1380

tcctgttacc agtggctgct gccagtggcg ataagtcgtg tcttaccggg ttggactcaa   1440

gacgatagtt accggataag gcgcagcggt cgggctgaac gggggggttcg tgcacacagc   1500

ccagcttgga gcgaacgacc tacaccgaac tgagatacct acagcgtgag ctatgagaaa   1560

gcgccacgct tcccgaaggg agaaaggcgg acaggtatcc ggtaagcggc agggtcggaa   1620

caggagagcg cacgagggag cttccagggg gaaacgcctg gtatctttat agtcctgtcg   1680

ggtttcgcca cctctgactt gagcgtcgat ttttgtgatg ctcgtcaggg gggcggagcc   1740

tatggaaaaa cgccagcaac gcggcctttt tacggttcct ggccttttgc tggccttttg   1800

ctcacatgtt ctttcctgcg ttatcccctg attctgtgga taaccgtatt accgcctttg   1860
```

-continued

```
agtgagctga taccgctcgc cgcagccgaa cgaccgagcg cagcgagtca gtgagcgagg   1920
aagcgtaccc gataaaagcg gcttcctgac aggaggccgt tttgttttgc agcccaccta   1980
gcggaagagc gcccaatacg caaaccgcct ctccccgcgc gttggccgat tcattaatgc   2040
agctggcacg acaggtttcc cgactggaaa gcgggcagtg agcgcaacgc aattaatgtg   2100
agttagctca ctcattaggc accccaggct ttacacttta tgctcccggc tcgtatgttg   2160
tgtggaattg tgagcggata acaattgaat tcaaggagtt aattatgaaa aaaaccgcga   2220
ttgcgattgc ggtggcgctg gcgggctttg cgaccgtggc ccaggcggcc tctagaatct   2280
gcggccgcac tagatataat taaggagata aatatgaaat atctgctgcc gaccgcggcg   2340
gcgggcctgc tgctgctggc ggcgcagccg gcgatggcgc tcgagtcaat actagtggcc   2400
aggccggcct tgaaactgtt gaaagttgtt tagcaaaacc ccatacagaa aattcattta   2460
ctaacgtctg gaaagacgac aaaactttag atcgttacgc taactatgag ggctgtctgt   2520
ggaatgctac aggcgttgta gtttgtactg gtgacgaaac tcagtgttac ggtacatggg   2580
ttcctattgg gcttgctatc cctgaaaatg agggtggtgg ctctgagggt ggcggttctg   2640
agggtggcgg ctctgagggt ggcggtacta aacctcctga gtacggtgat acacctattc   2700
cgggctatac ttatatcaac cctctcgacg gcacttatcc gcctggtact gagcaaaacc   2760
ccgctaatcc taatccttct cttgaggagt ctcagcctct taatactttc atgtttcaga   2820
ataataggtt ccgaaatagg cagggggcat taactgttta tacgggcact gttactcaag   2880
gcactgaccc cgttaaaact tattaccagt acactcctgt atcatcaaaa gccatgtatg   2940
acgcttactg gaacggtaaa ttcagagact gcgctttcca ttctggcttt aatgaggatc   3000
cattcgtttg tgaatatcaa ggccaatcgt ctgacctgcc tcaacctcct gttaatgctg   3060
gcggcggctc tggtggtggt tctggtggcg gctctgaggg tggtggctct gagggtggcg   3120
gttctgaggg tggcggctct gagggtggcg gttccggtgg tggctctggt tccggtgatt   3180
ttgattatga aaagatggca aacgctaata agggggctat gaccgaaaat gccgatgaaa   3240
acgcgctaca gtctgacgct aaaggcaaac ttgattctgt cgctactgat tacggtgctg   3300
ctatcgacgg tttcattggt gacgtttccg gccttgctaa tggtaatggt gctactggtg   3360
attttgctgg ctctaattcc caaatggctc aagtcggtga cggtgataat tcacctttaa   3420
tgaataattt ccgtcaatat ttaccttccc tccctcaatc ggttgaatgt cgcccttttg   3480
tctttggcgc tggtaaacca tatgaatttt ctattgattg tgacaaaata aacttattcc   3540
gtggtgtctt tgcgtttctt ttatatgttg ccacctttat gtatgtattt tcgacgtttg   3600
ctaacatact gcgtaataaa gagtcttaag ctagctaagc ggccgcatta ccgatcgccc   3660
ttcccaacag ttgcgcagcc tgaatggcga atgggacgcg ccctgtagcg gcgcattaag   3720
cgcggcgggt gtggtggtta cgcgcagcgt gaccgctaca cttgccagcg ccctagcgcc   3780
cgctcctttc gctttcttcc cttcctttct cgccacgttc gccggctttc cccgtcaagc   3840
tctaaatcgg gggctccctt tagggttccg atttagtgct ttacggcacc tcgaccccaa   3900
aaaacttgat tagggtgatg gttcacgtag tgggccatcg ccctgataga cggtttttcg   3960
ccctttgacg ttggagtcca cgttctttaa tagtggactc ttgttccaaa ctggaacaac   4020
actcaaccct atctcggtct attcttttga tttataaggg attttgccga tttcggccta   4080
ttggttaaaa aatgagctga tttaacaaaa atttaacgcg aattttaaca aaatattaac   4140
gcttacaatt tag                                                      4153
```

We claim:

[1. A phagemid vector comprising:

a selectable marker;

a ColE1 origin;

an f1 origin; and after the ColE1 origin but before the f1 origin, further comprising the following features:

a bacterial transcription terminator;

a promoter, a first ribosomal binding site;

a first leader sequence;

a first cloning region;

a second ribosomal binding site;

a second leader sequence;

a second cloning region for receiving a gene encoding a polypeptide to be displayed; and a nucleotide sequence encoding a product that enables display of a polypeptide on the surface of a phagemid particle.]

[2. A phagemid vector as in claim 1 wherein at least one of the first or second ribosomal binding sites comprises Seq. ID No. 13.]

3. [A phagemid vector as in claim 1] *A phagemid vector comprising:*

*a selectable marker;*

*a ColE1 origin;*

*an f1 origin; and*

*after the ColE1 origin but before the f1 origin, further comprising the following features: a bacterial transcription terminator and a promoter wherein the bacterial transcription terminator is upstream of the promoter;*

*a first ribosomal binding site;*

*a first leader sequence;*

*a first cloning region;*

*a second ribosomal binding site;*

*a second leader sequence;*

*a second cloning region for receiving a gene encoding a polypeptide to be displayed; and*

*a nucleotide sequence encoding a product that enables display of a polypeptide on the surface of a phagemid particle,* wherein at least one of the first or second leader sequences comprises a sequence selected from the group consisting of Seq. ID No. 14 and Seq. ID No. 17.

[4. A phagemid vector as in claim 1 wherein the nucleotide sequence encoding a product encodes a protein selected from the group consisting of pIII and pVIII.]

[5. A phagemid vector as in claim 1 wherein the nucleotide sequence encoding a product encodes a truncated pIII.]

[6. A phagemid vector as in claim 1 wherein the nucleotide sequence encoding a product encodes a synthetic pIII.]

[7. A phagemid vector as in claim 1 wherein the selectable marker is selected from the group consisting of ampicillin resistance, chloramphenicol transferase resistance, tetracycline resistance and kanamycin resistance.]

8. A phagemid vector comprising Seq. ID No. 18.

9. A vector comprising a sequence selected from the group consisting of Seq. ID Nos. 19, 20 and 21.

* * * * *